US008742047B2

(12) United States Patent
Lewandowski et al.

(10) Patent No.: US 8,742,047 B2
(45) Date of Patent: *Jun. 3, 2014

(54) POLYMERIZABLE IONIC LIQUID COMPRISING MULTIFUNCTIONAL CATION AND ANTISTATIC COATINGS

(75) Inventors: Kevin M. Lewandowski, Inver Grove Heights, MN (US); Larry R. Krepski, White Bear Lake, MN (US); Yizhong Wang, Woodbury, MN (US); Joel D. Oxman, Minneapolis, MN (US); Peiwang Zhu, Woodbury, MN (US); Brian N. Holmes, St. Paul, MN (US); Thomas P. Klun, Lakeland, MN (US); Bryan V. Hunt, Nowthen, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 43 days.

This patent is subject to a terminal disclaimer.

(21) Appl. No.: 13/380,252

(22) PCT Filed: Aug. 24, 2010

(86) PCT No.: PCT/US2010/046411
§ 371 (c)(1),
(2), (4) Date: Dec. 22, 2011

(87) PCT Pub. No.: WO2011/031442
PCT Pub. Date: Mar. 17, 2011

(65) Prior Publication Data
US 2012/0149800 A1  Jun. 14, 2012

Related U.S. Application Data

(60) Provisional application No. 61/237,992, filed on Aug. 28, 2009, provisional application No. 61/289,072, filed on Dec. 22, 2009.

(51) Int. Cl.
| | | |
|---|---|---|
| *C08F 26/00* | (2006.01) | |
| *C08F 12/30* | (2006.01) | |
| *C08F 2/46* | (2006.01) | |
| *C08J 3/28* | (2006.01) | |
| *A61K 6/00* | (2006.01) | |
| *C08F 118/02* | (2006.01) | |

(52) U.S. Cl.
USPC ........... 526/263; 526/287; 526/312; 526/319; 522/153; 522/150; 522/151; 522/152; 522/154; 522/179; 522/176; 522/182; 524/910; 524/912; 524/911

(58) Field of Classification Search
USPC ......... 522/113, 114, 116, 115, 117, 120, 121, 522/126, 129, 130, 150 M, 151, 152, 153, 522/154, 173, 176, 167, 150; 106/287.2, 106/287.29, 287.3; 252/8.91; 524/910, 911, 524/912; 526/263, 258, 287, 312, 319
See application file for complete search history.

(56) References Cited

U.S. PATENT DOCUMENTS

| | | |
|---|---|---|
| 3,250,808 A | 5/1966 | Moore, Jr. |
| 3,780,092 A | 12/1973 | Samour |
| 4,049,705 A | 9/1977 | Schwing |
| 4,262,072 A | 4/1981 | Wendling |
| 4,503,169 A | 3/1985 | Randklev |
| 4,619,979 A | 10/1986 | Kotnour |
| 4,843,134 A | 6/1989 | Kotnour |
| 4,872,936 A | 10/1989 | Engelbrecht |
| 4,933,405 A | 6/1990 | Evani |
| 5,063,257 A | 11/1991 | Akahane |
| 5,130,347 A | 7/1992 | Mitra |
| 5,154,762 A | 10/1992 | Mitra |
| 5,159,035 A | 10/1992 | Evani |
| 5,161,041 A | 11/1992 | Abileah |
| 5,175,030 A | 12/1992 | Lu |
| 5,183,597 A | 2/1993 | Lu |
| 5,227,413 A | 7/1993 | Mitra |
| 5,367,002 A | 11/1994 | Huang |
| 5,427,835 A | 6/1995 | Morrison |
| 5,501,707 A | 3/1996 | Schieferstein |
| 5,501,727 A | 3/1996 | Wang |
| 5,520,725 A | 5/1996 | Kato |
| 5,534,322 A | 7/1996 | Ueyama |

(Continued)

FOREIGN PATENT DOCUMENTS

| | | |
|---|---|---|
| DE | 2750030 | 5/1979 |
| EP | 0537774 | 4/1993 |

(Continued)

OTHER PUBLICATIONS

Nakajima et al. Preparation of thermally stable polymer electrolytes from imidazolium-type ionic liquid derivatives. Polymer 46 (2005), 11499-11504.*
Ohno, "Design of Ion Conductive Polymers Based on Ionic Liquids", Macromol. Symp. 2007, pp. 551-556.
Antonucci et al., "Synthesis, Characterization and Evalutaion of Novel, Anti-Bacterial Monomers for Dental and Biomedical Applications", vol. 50, No. 2, Aug. 16, 2009, pp. 132-133, [[retrieved from the internet]] <http://www.nist.gov/manuscript-publication-search.cfm?pub_901947>.
Abedin et al., "Ionic Liquids: The Link to High-Temperature Molten Salts?", Account of Chemical Research, 2007, 40, 1106-1113.
Akimoto et al., "Polymere Modellmembranen", Angew. Chemie, vol. 93, No. 1, 1981, pp. 108-109.

(Continued)

*Primary Examiner* — Sanza McClendon
(74) *Attorney, Agent, or Firm* — Carolyn A. Fischer

(57) ABSTRACT

A multifunctional polymerizable ionic liquid is described comprising an anion and a cationic group having at least two ethylenically unsaturated polymerizable groups, each bonded to the cationic group via a divalent non-alkyl linking group. The multifunctional linking groups independently comprise a heteroatom such as oxygen or nitrogen. The linking groups may independently comprise one or more linkages such as an amide, urea, or ether linkage and more typically a urethane or ester linkage. The ethylenically unsaturated polymerizable groups are typically (meth)acrylate groups. Coatings and coated articles are also described.

18 Claims, No Drawings

(56) References Cited

U.S. PATENT DOCUMENTS

| | | |
|---|---|---|
| 5,545,676 A | 8/1996 | Palazzotto |
| 5,626,654 A | 5/1997 | Breton |
| 5,637,646 A | 6/1997 | Ellis |
| 5,771,328 A | 6/1998 | Wortman |
| 5,783,120 A | 7/1998 | Ouderkirk |
| 5,788,749 A | 8/1998 | Breton |
| 5,804,610 A | 9/1998 | Hamer |
| 5,825,543 A | 10/1998 | Ouderkirk |
| 5,828,488 A | 10/1998 | Ouderkirk |
| 5,859,089 A | 1/1999 | Qian |
| 5,871,360 A | 2/1999 | Kato |
| 5,882,774 A | 3/1999 | Jonza |
| 5,919,551 A | 7/1999 | Cobb, Jr. |
| 5,925,715 A | 7/1999 | Mitra |
| 5,962,550 A | 10/1999 | Akahane |
| 5,965,632 A | 10/1999 | Orlowski |
| 6,030,606 A | 2/2000 | Holmes |
| 6,096,925 A | 8/2000 | Lee |
| 6,111,696 A | 8/2000 | Allen |
| 6,277,471 B1 | 8/2001 | Tang |
| 6,280,063 B1 | 8/2001 | Fong |
| 6,354,709 B1 | 3/2002 | Campbell |
| 6,372,829 B1 | 4/2002 | Lamanna |
| 6,387,981 B1 | 5/2002 | Zhang |
| 6,428,862 B1 | 8/2002 | Noguchi |
| 6,572,693 B1 | 6/2003 | Wu |
| 6,577,358 B1 | 6/2003 | Arakawa |
| 6,670,436 B2 | 12/2003 | Burgath |
| 6,730,156 B1 | 5/2004 | Windisch |
| 6,740,413 B2 | 5/2004 | Klun |
| 6,750,352 B2 | 6/2004 | Ono |
| 6,759,113 B1 | 7/2004 | Tang |
| 6,765,038 B2 | 7/2004 | Mitra |
| 7,074,463 B2 | 7/2006 | Jones |
| 7,090,721 B2 | 8/2006 | Craig |
| 7,090,722 B2 | 8/2006 | Budd |
| 7,156,911 B2 | 1/2007 | Kangas |
| 7,241,437 B2 | 7/2007 | Davidson |
| 7,269,327 B2 | 9/2007 | Tang |
| 7,269,328 B2 | 9/2007 | Tang |
| 7,345,137 B2 | 3/2008 | Hebrink |
| 7,452,924 B2 | 11/2008 | Aasen |
| 7,553,881 B2 | 6/2009 | Salz |
| 7,649,029 B2 | 1/2010 | Kolb |
| 7,674,850 B2 | 3/2010 | Karim |
| 2002/0057564 A1 | 5/2002 | Campbell |
| 2002/0137825 A1 | 9/2002 | Lamanna |
| 2003/0129421 A1 | 7/2003 | Terauchi |
| 2004/0054041 A1 | 3/2004 | Schmidt |
| 2004/0077775 A1 | 4/2004 | Audenaert |
| 2006/0216500 A1 | 9/2006 | Klun |
| 2007/0194275 A1 | 8/2007 | Masuda |
| 2008/0027231 A1 | 1/2008 | Armstrong |
| 2008/0051605 A1 | 2/2008 | Ricks-Laskoski |
| 2008/0070966 A1 | 3/2008 | Elder |
| 2008/0124555 A1 | 5/2008 | Klun |
| 2008/0125559 A1 | 5/2008 | Radosz |
| 2008/0134895 A1 | 6/2008 | Ruud |
| 2008/0182917 A1 | 7/2008 | Miyabayashi |
| 2008/0224089 A1 | 9/2008 | Pei |
| 2009/0017256 A1 | 1/2009 | Hunt |
| 2009/0060859 A1 | 3/2009 | Garcia Castro |
| 2009/0142562 A1 | 6/2009 | Miyagawa |
| 2009/0239969 A1 | 9/2009 | Orlowski |
| 2011/0076424 A1 | 3/2011 | Pellerite |
| 2011/0288227 A1 | 11/2011 | Lewandowski |
| 2012/0276503 A1* | 11/2012 | Wang et al. ............... 433/217.1 |

FOREIGN PATENT DOCUMENTS

| | | |
|---|---|---|
| EP | 0980682 | 2/2000 |
| EP | 1116769 | 7/2001 |
| EP | 1285947 | 2/2003 |
| EP | 2067797 | 6/2009 |
| GB | 2449926 | 12/2008 |
| JP | 5-98049 | 4/1993 |
| JP | 5-163317 | 6/1993 |
| JP | 6-128501 | 5/1994 |
| JP | 61-36355 | 5/1994 |
| JP | 6-180859 | 6/1994 |
| JP | 07-041528 | 2/1995 |
| JP | 9-268260 | 10/1997 |
| JP | 2002-105058 | 4/2002 |
| JP | 2004-006232 | 1/2004 |
| JP | 2004-255481 | 9/2004 |
| JP | 2005-223967 | 8/2005 |
| JP | 2005-255843 | 9/2005 |
| JP | 2006/137885 | 6/2006 |
| JP | 2007-112722 A * | 10/2007 |
| JP | 2007/308616 | 11/2007 |
| JP | 2007-320093 | 12/2007 |
| JP | 2009/049397 | 3/2009 |
| JP | 2009-149828 | 7/2009 |
| JP | 2009-179727 | 8/2009 |
| JP | 2009-209219 | 9/2009 |
| JP | 2009-227949 | 10/2009 |
| JP | 2009-263627 | 11/2009 |
| WO | WO 97/05182 | 2/1997 |
| WO | WO 01/30305 | 5/2001 |
| WO | WO 01/30306 | 5/2001 |
| WO | WO 01/30307 | 5/2001 |
| WO | WO 02/055011 | 7/2002 |
| WO | WO 03/063804 | 8/2003 |
| WO | WO 2006/026064 | 3/2006 |
| WO | WO 2006/053083 | 5/2006 |
| WO | WO 2007/030679 | 3/2007 |
| WO | WO 2007/030715 | 3/2007 |
| WO | WO 2008/021533 | 2/2008 |
| WO | WO 2009/029438 | 3/2009 |
| WO | WO 2009/134694 | 11/2009 |
| WO | WO 2010/070819 | 6/2010 |
| WO | WO 2011/025847 | 3/2011 |
| WO | WO 2011/025963 | 3/2011 |
| WO | WO 2011/087621 | 7/2011 |
| WO | WO 2011/146356 | 11/2011 |

OTHER PUBLICATIONS

Anderson et al., "Solubility of $CO_2$, $CH_4$, $C_2H_6$, $C_2H_4$, $O_2$, and $N_2$ in 1-Hexyl-3methylpyridinium Bis(trifluoromethylsulfonyl)imide: Comparison to Other Ionic Liquids", Accounts of Chemical Research, 2007, 40, 1208-1216.

Angell et al., "Parallel Developments in Aprotic and Protic Ionic Liquids: Physical Chemistry and Applications", Accounts of Chemical Research, 2007, 40, 1228-1236.

Baranyai et al., "Thermal Degradation of Ionic Liquids at Elevated Temperatures", Aust. J. Chem. 2004, 57, 145-147.

Bowyer et al., "Indium-Mediated Addition of 4-Bromocrotonic Acid to Aldehydes and Ketones—A Simple, High Yielding Route to α-Allyl-β-Hydroxy Carboxylic Acids", Aust. J. Chem. 2004, 57, 135-137.

Castner, Jr. et al., "Intermolecular Dynamics, Interactions, and Solvation in Ionic Liquids", Accounts of Chemical Research, 2007, 40, 1217-1227.

Diao et al., "High Performance Cross-Linked Poly(2-acrylamido-2-methylpropanesulfonic acid)-Based Proton Exchange Membranes for Fuel Cells", Macromolecules, vol. 43, Jul. 14, 2010, pp. 6398-6405.

Earle et al., "Keto-Enol Tautomerism as a Polarity Indicator in Ionic Liquids", Aust. J. Chem. 2004, 57, 149-150.

Fainerman-Melnikova et al., "Metal-Ion Recognition-Selective Bulk Membrane Transport of Silver(I) Using Thioether Donor Macrocycles as Ionophores, and X-Ray Structure of the Silver Complex of an $S_4$-Donor Ring", Aust. J. Chem. 2004, 57, 161-166.

Forsyth et al., "Ionic Liquids Based on Imidazolium and Pyrrolidinium Salts of the Tricyanomethanide Anion", Aust. J. Chem. 2004, 57, 121-124.

Forsyth et al., "Ionic Liquids—An Overview", Aust. J. Chem. 2004, 57, 113-119.

Friberg et al. "Copolymerization in a Non-Aqueous Lyotropic Liquid Crystal", Journal of Dispersion Science and Technology, vol. 14, No. 2, Jan. 1, 1993; 205-235.

(56) References Cited

OTHER PUBLICATIONS

Friberg et al., "Molecular Location in a Nonaqueous Lyotropic Liquid Crystal Polymer", Journal of Polymer Science, Part A, vol. 28, 1990, pp. 3575-3585.
Friberg, "Polyelectrolyte Synthesis in a Lamellar Liquid Crystal", Ber. Bundesges. Phys. Chem., vol. 100, No. 6, 1996, pp. 1083-1086.
Gou et al., "Measurement of the Dissolved Oxygen Concentration in Acryalte Monomers with a Novel Photochemical Methods", Journal of Polymer Science, Polym. Sci.: Part A: Polymer Chemistry, vol. 42, (2004), pp. 1285-1292.
Green et al., (2009) "The Design of Polymeric Ionic Liquids for the Preparation of Functional Materials", Polymer Reviews 49: 4, 339-360.
Guest Editorial, "Ionic Liquids", Accounts of Chemical Research, 2007, 40, 1077-1078.
Han et al., "Ionic Liquids in Separations", Accounts of Chemical Research, 2007, 40, 1079-1086.
Hardcare et al., "Structure and Solvation in Ionic Liquids", Accounts of Chemical Research, 2007, 40, 1146-1155.
Hemeon et al., Manganese Dioxide Allylic and Benzylic Oxidation Reactions in Ionic Liquids, Aust. J. Chem. 2004, 57, 125-128.
Hu et al., "Room-Temperature Ionic Liquids: Slow Dynamics, Viscosity, and the Red Edge Effect", Accounts of Chemical Research, 2007, 40, 1097-1105.
Ilesinghe et al., "An Evaluation of Some Hindered Diamines as Chiral Modifiers of Metal-Promoted Reactions", Aust. J.Chem. 2004, 57, 167-176.
Iwata et al., "Local Structure Formation in Alkyl-imidazolium-Based Ionic Liquids as Revealed by Linear and Nonlinear Raman Spectroscopy", Accounts of Chemical Research, 2007, 40, 1174-1181.
Jimenez et al., "Frontal Polymerization with Monofunctional and Difunctional Ionic Liquid Monomers", Journal of Polymer Science: Part A: Polymer Chemistry, vol. 45, 2745-2754 (2007).
Jimenez et al., "Photopolymerization Kinetics of Ionic Liquid Monomers Derived From the Neutralization Reaction Between Trialkylamines and Acid-Containing (Meth)Acrylates", Journal of Polymer Science: Part A: Polyer Chemistry, pp. 3009-3021 (Dec. 2006/Feb. 2007).
Juger et al., "Synthesis, Polymerization and Conducting Properties of an Ionic Liquid-Type Anionic Monomer", Tatrahedron Letters 50 (2009) 128-131.
Kapakoglou et al., "Coacervation of Surfact-Functionalized Polymerized Vesicles Derived from Ammonium Bromide Surfactants. Application to the Selective Speciation of Chromium in Environmental Samples", Anal. Chem., vol. 80, 2008, pp. 9787-9796.
Klee et al., "Monomers for low shrinking composites, $2^a$—Synthesis of branched methacrylates and their application in dental composites," Macromolecular Chemistry and Physics, vol. 200, Issue 3, pp. 517-523, (1999).
Lu et al., "Advanced Applications of Ionic Liquids in Polymer Science", Progress in Polymer Science 34, (2009), 431-448.
Lynden-Bell et al., "Simulations of Ionic Liquids, Solutions, and Surfaces", Accounts of Chemical Research, 2007, 40, 1138-1145.
MacFarlane et al., "Ionic Liquids in Electrochemical Devices and Processes: Managing Interfacial Electrochemistry", Accounts of Chemical Research, 2007, 40, 1165-1173.
Maginn, "Atomistic Simulation of the Thermodynamic and Transport Properties of Ionic Liquids", Accounts of Chemical Research, 2007, 40, 1200-1207.
Mathis et al., "Properties of a New Glass Ionomer/Composite Resin Hybrid Restorative", Abstract No. 51, J. Dent. Res., 66: 113 (1987).
Matijevic, Surface & Colloid Science, vol. 6 ed., Wiley Interscience (1973), pp. 23-29.
Meindersma et al., "Ionic Liquids", Ullmann's Encyclopedia of Industrial Chemistry, 2007.
Mosmuller et al., "Lipase Activity in Vesicular Systems: Characterization of *Candida cylindracea* Lipase and Its Activity in Polymerizable Dialkylammonium Surfactant Vesicles", Biotechnology and Bioengineering, vol. 42, 1993, 196-204.

Nakajima, "Preparation of Termally Stable Polymer Electrolytes From Imidazolium-Type Ionic Liquid Derivatives", Science Direct, Polymer 46 (2005) 11499-11504.
Ohno et al., "Amino Acid Ionic Liquids", Accounts of Chemical Research 2007, 40, 1122-1129.
Ohno et al., "Development of new class of ion conductive polymers based on ionic liquids", Electrochimica ACTA, vol. 50, No. 2-3, Nov. 30, 2004, pp. 254-260.
Olivier-Bourbigou et al.; "Ionic Liquids and Catalysis: Recent Progress From Knowledge to Applications", Applied Catalysis A: General 373 (2010) 1-56.
Padua et al., Molecular Solutes in Ionic Liquids: A Structural Perspective, Accounts of Chemical Research, 2007, 40, 1087-1096.
Plechkova et al., "Applications of ionic liquids in the chemical industry", Chemical Society Reviews, 2008, 37, pp. 123-150.
Popolo et al., "Clusters, Liquids and Crystals of Dialkyimidazolium Salts. A Combined Perspective from ab Initio and Classical Computer Simulations", Accounts of Chemical Research, 2007, 40, 1156-1164.
Rebelo et al., "Accounting for the Unique Double Dual Nature of Ionic Liquids from a Molecular Thermodynamic and Modeling Standpoint", Accounts of Chemical Research, 2007, 40, 1114-1121.
Ruckenstein et al., "Binding Catalytic Sites to the Surface of Porous Polymers and Some Catalytic Application", Chem. Mater. 1992, vol. 4, pp. 122-127.
Shim et al., "Solvation, Solute Rotation and Vibration Relaxation, and Electrom-Transfer Reactions in Room-Temperature Ionic Liquids", Accounts of Chemical Research 2007, 40, 1130-1137.
Smiglak et al., "The Second Evolution of Ionic Liquids: From Solvents and Separations to Advanced Materials—Energetic Examples From the Ionic Liquid Cookbook", Accounts of Chemical Research 2007, 40, 1182-1192.
Soulivong et al., "A Long-Chain Phosphine Designed as a Metallomesogen Generator—Synthesis and Coordination Properties", Aust. J. Chem. 2004, 57, 157-160.
Tan et al., "Photopolymerization and Characteristics of Reactive Organoclay-Polyurethane Nanocomposites", Polymer Composites, vol. 30, No. 5, Oct. 20, 2008, pp. 612-618.
Torimoto et al., "New Frontiers in Materials Science Opened by Ionic Liquids", Adv. Mater. 2009, 21, 1-26.
Tundo et al., Functionally Polymerized Surfactant Vesicles. Synthesis and Characterization, J. Am. Chem. Soc., vol. 104, 1982, pp. 456-461.
Vijayaraghavan et al., "Charge Transfer Polymerization in Ionic Liquids", Aust. J. Chem. 2004, 57, 129-133.
Wang et al., "Understanding Ionic Liquids through Atomistic and Coarse-Grained Molecular Dynamics Simulations", Accounts of Chemical Research, 2007, 40, 1193-1199.
Watts et al., "Determination of Polymerization Shrinkage Kinetics in Visible Light-Cured Materials: Methods Development", Dental Materials Oct. 1991, pp. 281-286.
Whitehead et al., "Analysis of Gold in Solutions Containing Ionic Liquids by Inductively Coupled Plasma Atomic Emission Spectrometry", Aust. J. Chem. 2004, 57, 151-155.
Yoshizawa et al., "Design of Ionic Liquids for Electrochemical Applications", Aust. J. Chem. 2004, 57, 139-144.
Yoshizawa et al., "Novel Polymer Electrolytes Prepared by Copolymerization of Ionic Liquid Monomers", Polymers For Advanced Technologies 13, 589-594 (2002).
Zaderenko, et al., "Synthesis and Regioselective Hydrolysis of 2-Imidazol-1-ylsuccinic Esters," Journal of Organic Chemistry, vol. 59, Issue 21, pp. 6268-6273, (1994).
The Dental Advisor; 3M ESPE Filtek™ Z250 Universal Restorative 9-year Clinical Performance+++++; Jun. 2008, 2 pages.
International Search Report PCT/US2010/046411, Sep. 6, 2011, 7 pgs.

* cited by examiner

POLYMERIZABLE IONIC LIQUID COMPRISING MULTIFUNCTIONAL CATION AND ANTISTATIC COATINGS

CROSS REFERENCE TO RELATED APPLICATIONS

This application is a national stage filing under 35 U.S.C. 371 of PCT/US2010/046411, filed Aug. 24, 2010, which claims priority to U.S. Provisional Application No. 61/237,992, filed Aug. 28, 2009 and U.S. Provisional Application No. 61/289,072, filed Dec. 22, 2009, the disclosure of which is incorporated by reference in their entirety herein.

BACKGROUND

Ionic liquids (ILs) are salts in which the cation and anion are poorly coordinated. At least one of the ionic components is organic and one of the ions has a delocalized charge. This prevents the formation of a stable crystal lattice, and results in such materials existing as liquids, often at room temperature, and at least, by definition, at less than 100° C. For example, sodium chloride, a typical ionic salt, has a melting point of about 800° C., whereas the ionic liquid N-methylimidazolium chloride has a melting point of about 75° C.

Ionic liquids typically comprise an organic cation, such as a substituted ammonium or a nitrogen-containing heterocycle, such as a substituted imidazolium, coupled with an inorganic anion. However, species have also been described wherein the cation and anion are organic. When the ionic liquid comprises at least one polymerizable group, such ionic liquid is a polymerizable ionic liquid ("PIL").

SUMMARY

Although various polymerizable ionic liquids have been described, industry would find advantage in new multifunctional polymerizable ionic liquids.

In one embodiment, a multifunctional polymerizable ionic liquid is described comprising an anion and a cationic group having at least two ethylenically unsaturated polymerizable groups, each bonded to the cationic group via a divalent non-alkyl linking group. The multifunctional linking groups independently comprise a heteroatom such as oxygen or nitrogen. The linking groups may independently comprise one or more linkages such as an amide, urea, or ether linkage and more typically a urethane or ester linkage. The ethylenically unsaturated polymerizable groups are typically (meth)acrylate groups.

In another embodiment, an (e.g. antistatic) coating is described comprising any of the multifunctional polymerizable ionic liquids described herein alone or in combination with other (meth)acrylate components such as a monofunctional (e.g. mono(meth)acrylate) polymerizable ionic liquid.

In yet another embodiment, a coated substrate is described comprising a (e.g. film) substrate and the coating described herein cured on a surface of the substrate.

In yet another embodiment, a multifunctional polymerizable ionic liquid comprising an initiator is described, having an air to nitrogen curing exotherm ratio of at least 0.70. The polymerizable ionic liquid comprises at least one ethylenically unsaturated polymerizable group bonded to a cationic group via a divalent non-alkyl linking group. When the multifunctional polymerizable ionic liquid has a sufficiently high air to nitrogen curing exotherm ratio, the polymerizable ionic liquid can be cured in air, rather than requiring curing in the absence of oxygen such as by curing in the presence of nitrogen.

DETAILED DESCRIPTION OF ILLUSTRATIVE EMBODIMENTS

Presently described are polymerizable ionic liquids, comprising a cation and an anion that are poorly coordinated. Such polymerizable ionic liquids have a melting point ($T_m$) below about 100° C. The melting point of these compounds is more preferably below about 60° C., 50° C., 40° C., or 30° C. and most preferably below about 25° C., for ease of use in various polymerizable compositions such as (e.g. antistatic) coatings with or without the aid of solvent carriers in the coating formulation. Polymerizable ionic liquids having a melting point below 25° C. are liquids at ambient temperature.

Suitable cationic groups, also known as onium salts, include substituted ammonium salts, substituted phosphonium salts, and substituted imidazolium salts. The structures of the cations of such onium salts are depicted as follows:

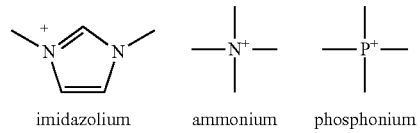

imidazolium    ammonium    phosphonium

The anion may be organic or inorganic, and is typically a monovalent anion, i.e. having a charge of −1.

The polymerizable ionic liquids described herein comprise at least two polymerizable groups, and thus are described as multifunctional polymerizable ionic liquids, rather than monofunctional polymerizable ionic liquid having a single polymerizable group. The polymerizable ionic liquids typically comprise two or three polymerizable groups. The polymerizable groups are ethylenically unsaturated terminal polymerizable groups including (meth)acryl such as (meth)acrylamide ($H_2C$=CHCON— and $H_2C$=CH($CH_3$)CON—) and (meth)acrylate($CH_2$CHCOO— and $CH_2C(CH_3)$COO—). Other ethylenically unsaturated polymerizable groups include vinyl ($H_2C$=C—) including vinyl ethers ($H_2C$=CHOCH—).

The polymerizable ionic liquid functional as a reactive monomer and thus is substantially unpolymerized in the curable (e.g. antistatic) coating composition at the time the curable composition is applied to a (e.g. film) substrate. The curable composition hardens upon curing via polymerization of the ethylenically unsaturated groups of the multifunctional polymerizable ionic liquid.

The multifunctional polymerizable ionic liquids described herein can be characterized as having a multifunctional cation, having two or more polymerizable groups, each bonded to the same cationic group via a divalent non-alkyl linking group. As used herein, linking groups refer to the entirety of the chain of atoms between the (e.g. single) cation and ethylenically unsaturated terminal group. Although the linking groups may and often comprises lower alkyl segments, e.g. of 1 to 4 carbon atoms, the linking groups further comprise other atoms within the carbon backbone and/or other groups pendant to the (e.g. carbon) backbone. Most commonly, the linking groups comprise heteroatoms such as sulfur, oxygen, or nitrogen, and more commonly oxygen or nitrogen. The linking groups may comprise linkages such as amide (—CONR—), urea (—RNCONR—) or ether (—COC—) linkages and more commonly urethane (—ROCONR—) or ester linkages (—COOR)—; wherein R is a lower alkyl of 1-4 carbon atoms.

For embodiments wherein the cation is ammonium or phosphonium, the polymerizable ionic liquid may have the general formula:

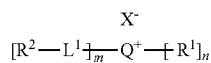

wherein:
Q is nitrogen or phosphorous
$R^1$ is independently hydrogen, alkyl, aryl, alkaryl, or a combination thereof;
$R^2$ is independently an ethylenically unsaturated group;
$L^1$ is independently a linking group with the proviso that at least two of the linking groups are not alkyl linking groups;
m is an integer of 2 to 4;
n is an integer of 0 to 2;
and m+n=4; and
X is an anion.

At least two of the linking groups, $L^1$, are preferably linking groups that comprise one or more heteroatoms such as nitrogen, oxygen, or sulfur. In favored embodiments, at least two of the linking groups, $L^1$ comprise nitrogen or oxygen heteroatoms, such as linking groups that comprise an amide, urea, ether, urethane or ester linkage. The linking group may comprise more than one of such linkages.

Although each terminal ethylenically unsaturated group, $R^2$, bonded to each linking group can comprise a different ethylenically unsaturated group, the terminal ethylenically unsaturated group, $R^2$, is typically the same ethylenically unsaturated polymerizable group, such as the same vinyl, (meth)acrylamide, or (meth)acrylate group.

In some embodiments, m is 3 and thus, the polymerizable ionic liquid is a trifunctional (e.g. tri(meth)acrylate) polymerizable ionic liquid. In other embodiments, m is 2 and thus, the polymerizable ionic liquid is a difunctional (e.g. di(meth)acrylate) polymerizable ionic liquid.

In some embodiments, n is at least 1. $R^1$ is typically hydrogen or a straight-chain lower alkyl of 1 to 4 carbon atoms. However, $R^1$ may optionally be branched or comprise a cyclic structure. $R^1$ may optionally comprise phosphorous, halogen, one or more heteroatoms such as nitrogen, oxygen, or sulfur.

Illustrative examples of anions useful herein include various organic anions such as carboxylates ($CH_3CO_2^-$, $C_2H_5CO_2^-$, $ArCO_2^-$), sulfates ($HSO_4^-$, $CH_3SO_4^-$), sulfonates ($CH_3SO_3^-$), tosylates, and fluoroorganics ($CF_3SO_4^-$, $(CF_3SO_2)_2N^-$, $(C_2F_5SO_2)_2N^-$, $(C_2F_5SO_2)$ $(CF_3SO_2)N^-$, $CF_3CO_2^-$, $CF_3C_6F_4SO_3^-$, $CH_3C_6F_4SO_3^-$, tetrakis(pentafluorophenyl)borate). The anion may alternatively be an inorganic anion such as $ClO_4^-$, fluoroinorganics ($PF_6^-$, $BF_4^-$, $AsF_6^-$, $SbF_6^-$) and halides ($Br^-$, $I^-$, $Cl^-$). In some embodiments, the anion is preferably a sulfonate. Such illustrative anions lack ethylenically unsaturated groups and thus are non-polymerizable anions.

Preferred polymerizable ionic species wherein the cation is ammonium include:

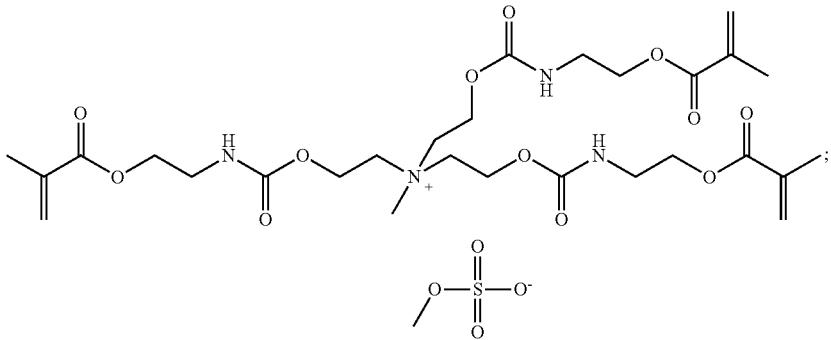

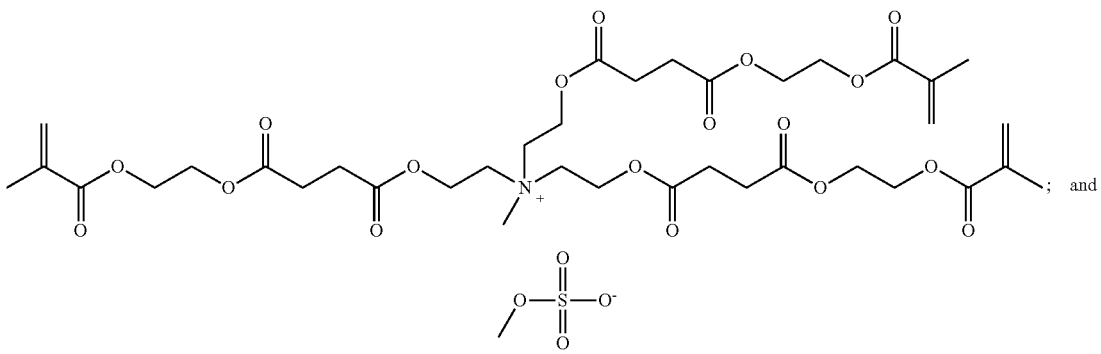

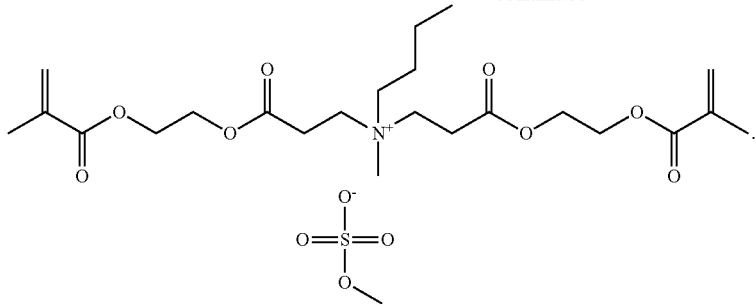

These species just described can include various other anions, such as a fluororganic anion.

For embodiments wherein the cation is imidazolium, the polymerizable ionic liquid may have the general formula:

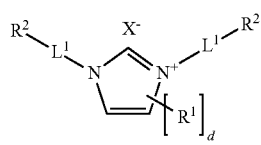

wherein
X, $R^1$, $L^1$ and $R^2$ are the same as previously described;
and d is an integer of 0 to 3.

Although the polymerizable groups are depicted as being bonded via the linking group to the nitrogen atoms of the imidazolium cation, one or both polymerizable groups can optionally be bonded via the linking group, $L^1$, at other positions of the imidazolium ring.

A preferred polymerizable ionic species wherein the cation is imidazolium includes stantially completely cured in air (i.e. an oxygen rich environment) rather than requiring curing in the absence of oxygen.

For embodiments wherein the composition is to be cured in air and the multifunctional polymerizable ionic liquid is combined with a different e.g. (meth)acrylate such as a monofunctional polymerizable ionic liquid, that exhibits a high air to nitrogen curing exotherm ratio, the air to oxygen curing exotherm ratio of the multifunctional polymerizable ionic liquid, described herein, may be even lower than 0.70.

One suitable monofunctional polymerizable ionic liquid that can be combined with a multifunctional polymerizable ionic liquid is (acryloyloxyethyl)-N,N,N-trimethylammonium bis (trifluoromethanesulfonyl)imide) having an air to nitrogen curing exotherm ratio of about 0.98.

A completely cured (i.e. hardened) polymerizable ionic liquid is solid at 25° C. and is substantially free of uncured polymerizable ionic liquid. When uncured polymerizable ionic liquid is present it typically results as a surface residue exhibiting a "wet" appearance. Minimal surface inhibition not only provides more complete curing but also minimizes the formation of a less cured oxygen inhibited surface layer.

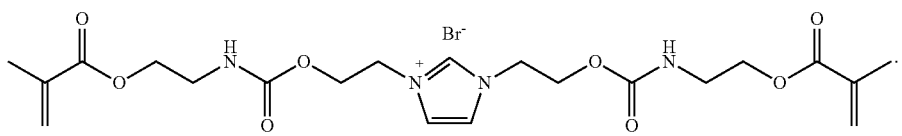

Preferred multifunctional polymerizable ionic liquids exhibit a high air to nitrogen curing exotherm ratio, as can be measured by photo DSC according to the test method described in the examples. The air to nitrogen curing ratio is typically at least 0.70 or 0.75. In preferred embodiments, the air to nitrogen curing exotherm ratio is typically at least the 0.80, 0.85, 0.90, or 0.95. Although the exemplified compositions were cured in the presence of nitrogen, it has been found that when the air to nitrogen curing ratio is sufficiently high, the polymerizable ionic liquid can advantageously be sub- The extent of curing can be determined by various methods known in art. One common method is to determine the amount of uncured material by solvent extraction. In preferred embodiments, the amount of uncured extractable polymerizable ionic liquid is less than 10%, more preferably less than 5%, and most preferably less than 1% by weight of the cured composition.

The polymerizable ionic liquids described herein can be made by several methods. One method includes reaction of a hydroxyl functional ionic precursor with a polymerizable isocyanate such as depicted by the following reaction scheme:

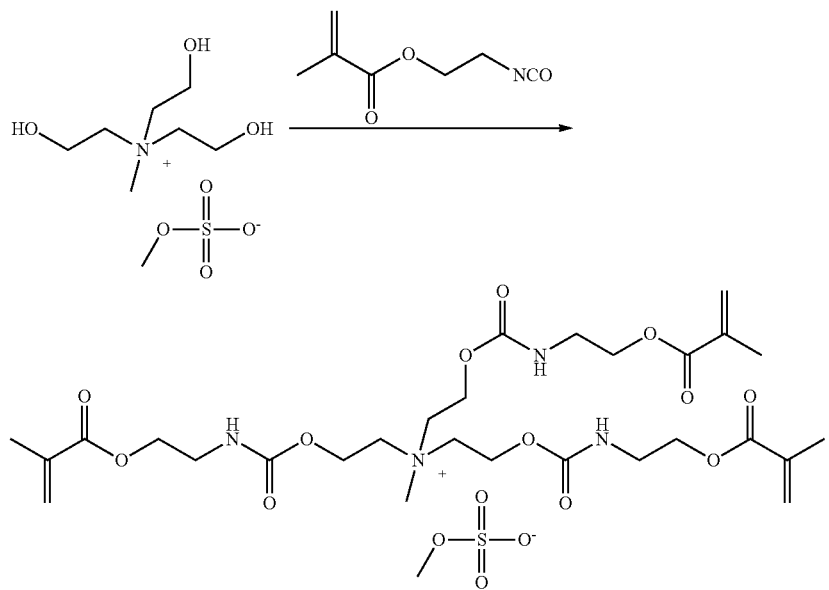

Commercially available starting materials include tris-(2-hydroxyethyl)-methyl ammonium methyl sulfate available from BASF (BASIONIC FS01), diethanolamine hydrochloride, 2-amino-1,3-propanediol hydrochloride, and tris(hydroxymethyl) aminomethane hydrochloride. The ionic product may be further reacted to exchange the anion using anion metathesis as described in "Ionic Liquids", Meindersma, G. W., Maase, M., and De Haan, A. B., Ullmann's Encyclopedia of Industrial Chemistry, 2007.

Another method includes the reaction of a hydroxyl functional amine precursor with a polymerizable isocyanate, followed by alkylation or acidification, such as depicted by the following reaction scheme:

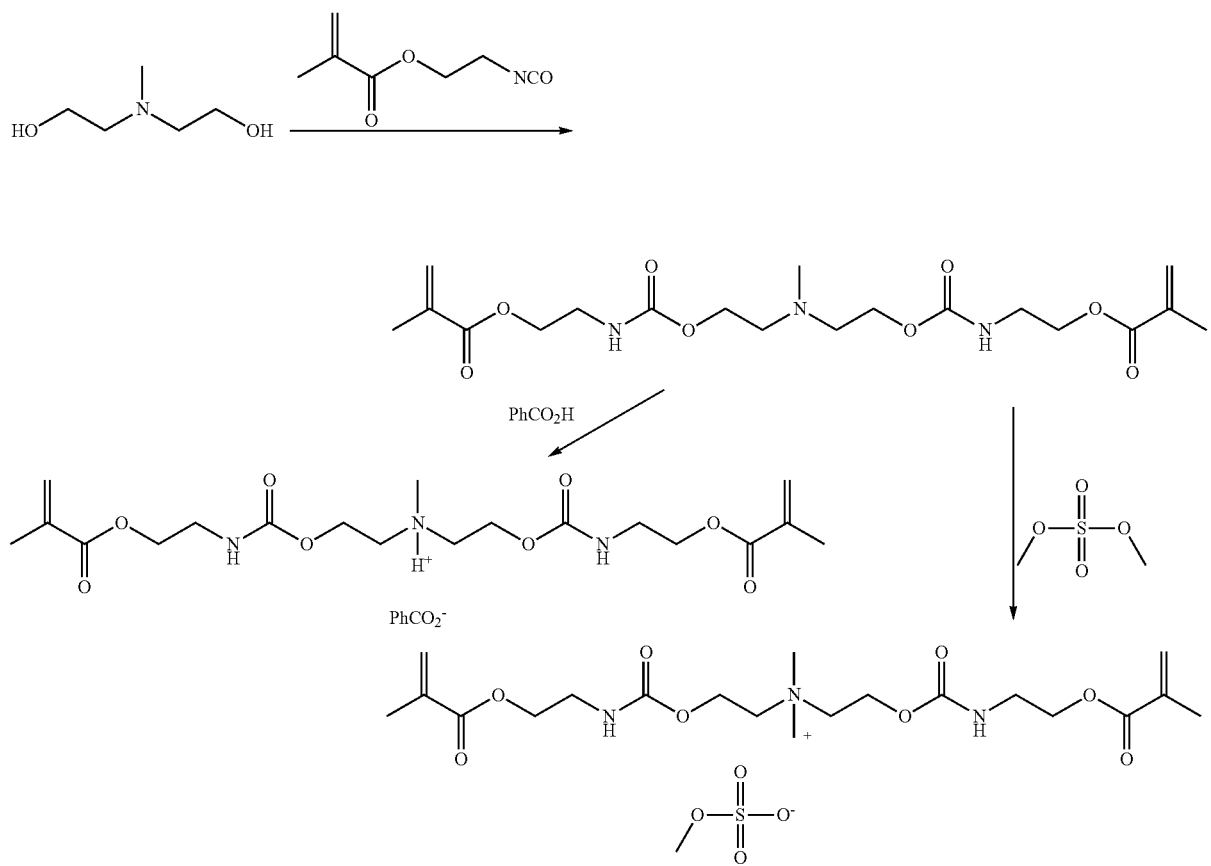

Commercially available starting materials include diethanol amine, diisopropanol amine, N-methyldiethanol amine, N-ethyldiethanol amine, N-butyldiethanol amine, triethanol amine, 1-[N,N-bis(2-hydroxyethyl)-amino]-2-propanol, triisopropanol amine, 3-amino-1,2-propanediol, 3-(dimethylamino)-1,2-propanediol, 3-(diethylamino)-1,2-propanediol, 3-(dipropylamino)-1,2-propanediol, 3-(diisopropylamino)1,2,-propanediol, 2-amino-1,3-propanediol, 2-amino-2-ethyl-1,3,-propanediol, 2-amino-2-methyl-1,3,-propanediol, tris(hydroxymethyl)amino methane, bis(2-hydroxyethyl)amino-tris(hydroxymethyl)methane, 2,2-bis(hydroxymethyl)-2,2',2''-nitrilotriethanol, N,N'bis(2-hydroxyethyl)-ethylenediamine, N—N—N'—N'-tetrakis(2-hydroxypropyl)-ethylenediamine, 1,3-bis[tris(hydroxymethyl)-methylamino]propane, 3-pyrrolidino-1,2-propanediol, 3-piperidino-1,2-propanediol, and 1,4-bis(2-hydroxyethyl)-piperazine.

Useful alkylating agents include alkyl halides, sulfates, and phosphonate esters, such as methyl iodide, ethyl iodide, methyl bromide, ethyl bromide, dimethyl sulfate, diethyl sulfate, and dimethyl methylphosphonate. Useful acidification agents include carboxylic acids, organosulfonic acids, and organophosphonic acids and inorganic acids such as hydrochloric acid, hydrofluoric acid, hydrobromic acid, phosphoric acid, nitric acid and the like.

Another method includes the reaction of an amine with an acrylate compound to give a polymerizable amine precursor, followed by alkylation or acidification, such as depicted by the following reaction scheme:

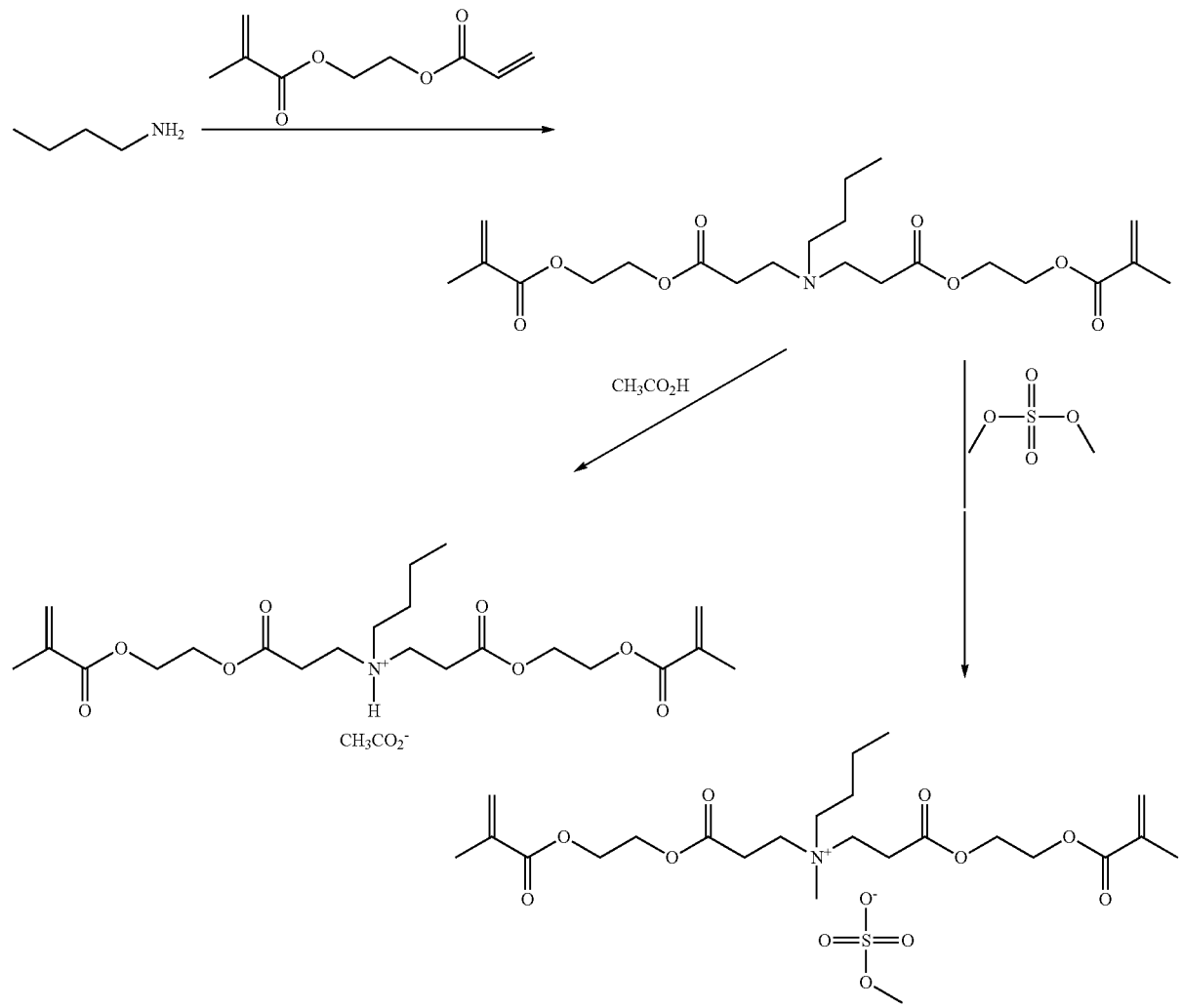

Commercially available starting materials include amines such as methylamine, ethylamine, propylamine, butylamine, hexylamine, isopropylamine, isobutylamine, 1-methylbutylamine, 1-ethy propylamine, 2-methylbutylamine, isoamylamine, 1,2-dimethylpropylamine, 1,3-dimethylbutylamine, 3,3-dimethylbutylamine, 2-aminoheptane, 3-aminoheptane, 1-methylheptyamine, 2-ethylhexylamine, 1,5-dimethylhexylamine, cyclopropylamine, cyclohexylamine, cyclobutylamine, cyclopentylamine, cycloheptylamine, cyclooctylamine, 2-aminonorbornane, 1-adamantanamine, allylamine, tetrahydrofurfurylamine, ethanolamine, 3-amino-1-propanol, 2-(2-aminoethoxy)ethanol, benzylamine, phenethylamine, 3-phenyl-1-propylamine, 1-aminoindan, ethylenediamine, diaminopropane, and hexamethylenediamine.

Another method, that provides a polymerizable ionic liquid containing an ether linking group, includes the reaction of a hydroxyl functional precursor with a functionalized (meth) acrylate molecule such as depicted by the following reaction scheme:

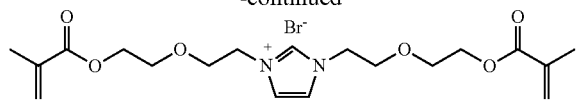

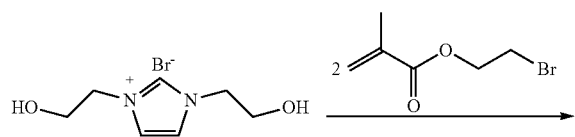

Another method, that provides a polymerizable ionic liquid containing an amide linking group, includes the reaction of an amine functional precursor with a functionalized (meth)acrylate molecule such as depicted by the following reaction scheme:

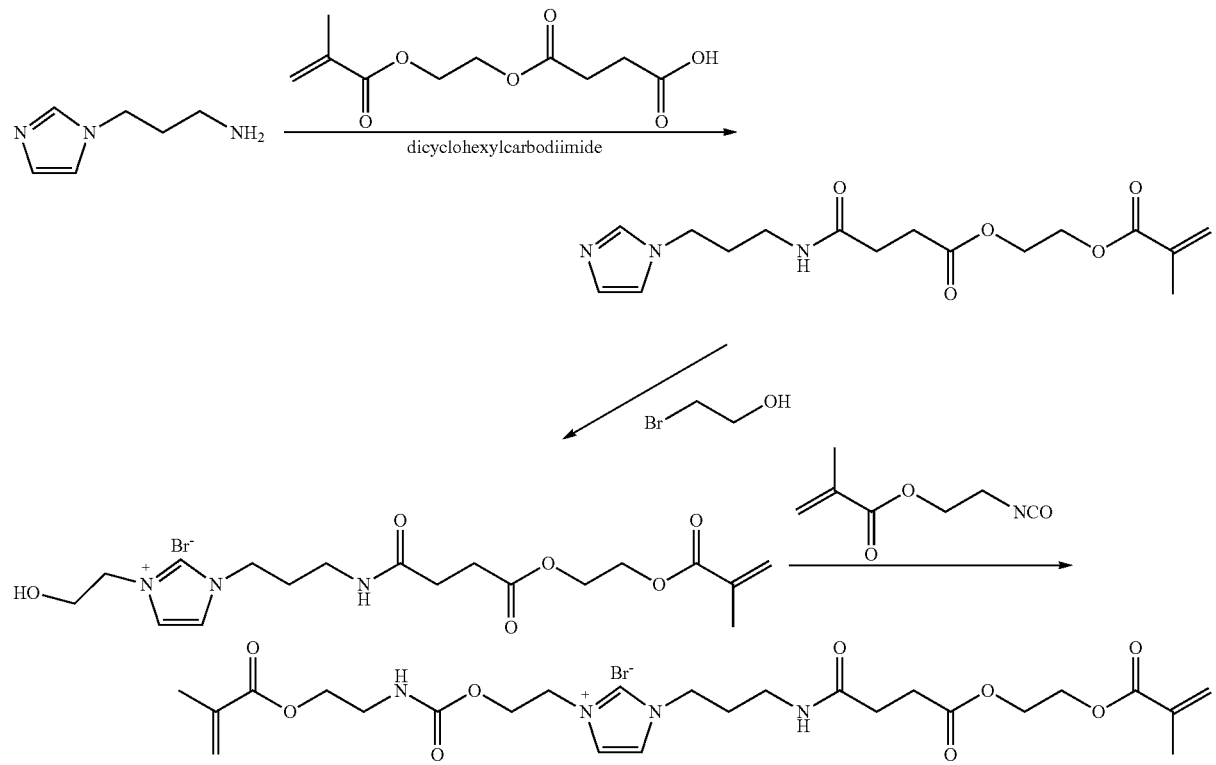

Another illustrative method, that provides a polymerizable ionic liquid containing a urea linking group, is depicted by the following reaction scheme:

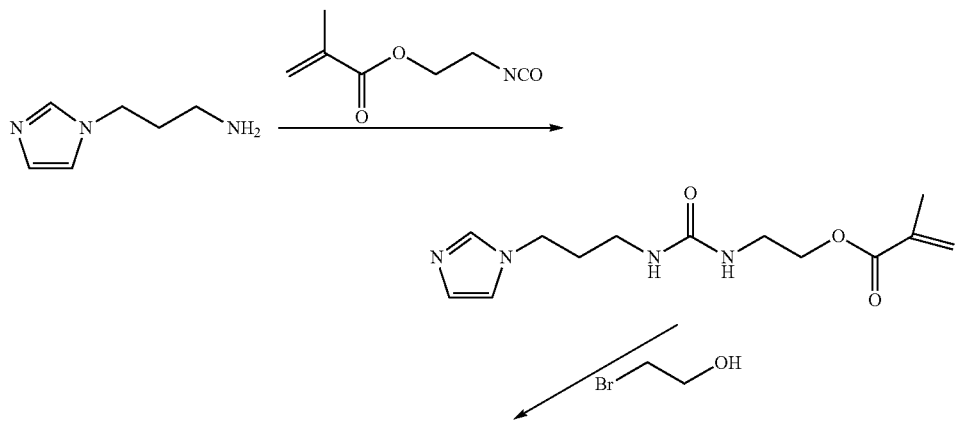

-continued

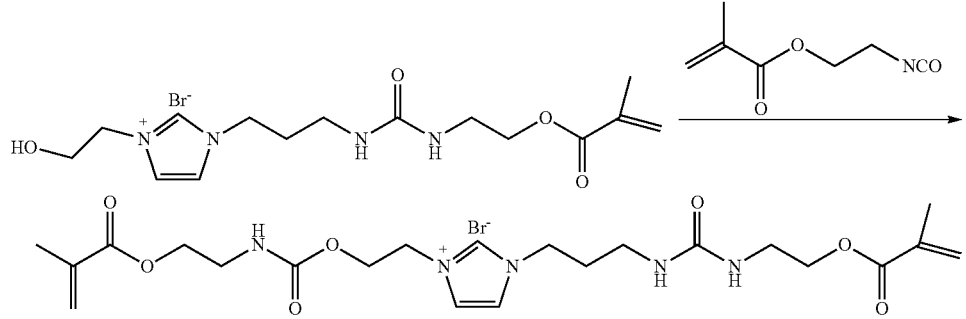

The polymerizable ionic liquids described herein, having a multifunctional cation (i.e. a cation having two or more ethylenically unsaturated groups) can be utilized in various polymerizable compositions such as an antistatic coating useful for making an antistatic layer of an optical film.

In some embodiments, the antistatic coating is comprised of a polymerizable ionic liquid having a multifunctional cation, as described herein, in the absence of any other ethylenically unsaturated polymerizable (e.g. (meth)acrylate) components.

In other embodiments, the antistatic layer comprises a combination of at least one polymerizable ionic liquid having a multifunctional cation, as described herein in combination with at least one monofunctional (e.g. mono(methacrylate)) polymerizable ionic liquid. In yet other embodiments, the antistatic layer further comprises at least one polymerizable silicone monomer, oligomer, or polymer. The polymerizable ionic liquid(s) may be present in the antistatic layer at a weight percentage of 1 to 99.95%, 10 to 60%, or 30 to 50%. The acrylate functional onium salts are preferred over the methacrylate onium salts because they exhibit a faster and greater degree of cure.

In either embodiment, an initiator is typically added to the multifunctional polymerizable ionic liquid or to the mixture of polymerizable ingredients comprising at least one multifunctional polymerizable ionic liquid, as described herein. The initiator is sufficiently miscible with the resin system to permit ready dissolution in (and discourage separation from) the polymerizable composition. It is appreciated that anion of the polymerizable ionic liquid can affect the solubility of the polymerizable ionic liquid, particularly with the initiator systems. When the polymerizable ionic liquid includes a fluororganic anion, care is taken to select an appropriate class and concentration of initiator.

Typically, the initiator is present in the composition in effective amounts, such as from about 0.1 weight percent to about 5.0 weight percent, based on the total weight of the composition.

In some embodiments, the multifunctional polymerizable ionic liquid or composition comprising such is photopolymerizable and the composition contains a photoinitiator (i.e., a photoinitiator system) that upon irradiation with actinic radiation initiates the polymerization (or hardening) of the composition. Such photopolymerizable compositions can be free radically polymerizable. The photoinitiator typically has a functional wavelength range from about 250 nm to about 800 nm.

Suitable photoinitiators (i.e., photoinitiator systems that include one or more compounds) for polymerizing free radically photopolymerizable compositions include binary and tertiary systems. Typical tertiary photoinitiators include an iodonium salt, a photosensitizer, and an electron donor compound as described in U.S. Pat. No. 5,545,676 (Palazzotto et al.). Iodonium salts include diaryl iodonium salts, e.g., diphenyliodonium chloride, diphenyliodonium hexafluorophosphate, and diphenyliodonium tetrafluoroboarate. Some preferred photosensitizers include monoketones and diketones (e.g. alpha diketones) that absorb some light within a range of about 300 nm to about 800 nm (preferably, about 400 nm to about 500 nm) such as camphorquinone, benzil, furil, 3,3,6,6-tetramethylcyclohexanedione, phenanthraquinone and other cyclic alpha diketones. Of these camphorquinone is typically preferred. Preferred electron donor compounds include substituted amines, e.g., ethyl 4-(N,N-dimethylamino)benzoate.

Other suitable photoinitiators for polymerizing free radically photopolymerizable compositions include the class of phosphine oxides that typically have a functional wavelength range of about 380 nm to about 1200 nm. Preferred phosphine oxide free radical initiators with a functional wavelength range of about 380 nm to about 450 nm are acyl and bisacyl phosphine oxides.

Commercially available phosphine oxide photoinitiators capable of free-radical initiation when irradiated at wavelength ranges of greater than about 380 nm to about 450 nm include bis(2,4,6-trimethylbenzoyl)phenyl phosphine oxide (IRGACURE 819, Ciba Specialty Chemicals, Tarrytown, N.Y.), bis(2,6-dimethoxybenzoyl)-(2,4,4-trimethylpentyl) phosphine oxide (CGI 403, Ciba Specialty Chemicals), a 25:75 mixture, by weight, of bis(2,6-dimethoxybenzoyl)-2,4,4-trimethylpentyl phosphine oxide and 2-hydroxy-2-methyl-1-phenylpropan-1-one (IRGACURE 1700, Ciba Specialty Chemicals), a 1:1 mixture, by weight, of bis(2,4,6-trimethylbenzoyl)phenyl phosphine oxide and 2-hydroxy-2-methyl-1-phenylpropane-1-one (DAROCUR 4265, Ciba Specialty Chemicals), and ethyl 2,4,6-trimethylbenzylphenyl phosphinate (LUCIRIN LR8893X, BASF Corp., Charlotte, N.C.).

Tertiary amine reducing agents may be used in combination with an acylphosphine oxide. Illustrative tertiary amines useful in the invention include ethyl 4-(N,N-dimethylamino)benzoate and N,N-dimethylaminoethyl methacrylate. When present, the amine reducing agent is present in the photopolymerizable composition in an amount from about 0.1 weight percent to about 5.0 weight percent, based on the total weight of the composition.

In some embodiments, the curable dental composition may be irradiated with ultraviolet (UV) rays. For this embodiment, suitable photoinitiators include those available under the trade designations IRGACURE and DAROCUR from Ciba Specialty Chemical Corp., Tarrytown, N.Y. and include 1-hydroxy cyclohexyl phenyl ketone (IRGACURE 184), 2,2- dimethoxy-1,2-diphenylethan-1-one (IRGACURE 651), bis (2,4,6-trimethylbenzoyl)phenylphosphineoxide (IRGACURE 819), 1-[4-2-hydroxyethoxy)phenyl]-2-hydroxy-2-methyl-1-propane-1-one (IRGACURE 2959), 2-benzyl-2-dimethylamino-1-(4-morpholinophenyl)butanone (IRGACURE 369), 2-methyl-1-[4-(methylthio)phenyl]-2-morpholinopropan-1-one (IRGACURE 907), and 2-hydroxy-2-methyl-1-phenyl propan-1-one (DAROCUR 1173).

The photopolymerizable compositions are typically prepared by admixing the various components of the compositions. For embodiments wherein the photopolymerizable compositions are not cured in the presence of air, the photoinitiator is combined under "safe light" conditions (i.e., conditions that do not cause premature hardening of the composition). Suitable inert solvents may be employed if desired when preparing the mixture. Examples of suitable solvents include acetone and dichloromethane.

Hardening is affected by exposing the composition to a radiation source, preferably a visible light source. It is convenient to employ light sources that emit actinic radiation light between 250 nm and 800 nm (particularly blue light of a wavelength of 380-520 nm) such as quartz halogen lamps, tungsten-halogen lamps, mercury arcs, carbon arcs, low-, medium-, and high-pressure mercury lamps, plasma arcs, light emitting diodes, and lasers. In general, useful light sources have intensities in the range of 0.200-1000 W/cm$^2$. A variety of conventional lights for hardening such compositions can be used.

The exposure may be accomplished in several ways. For example, the polymerizable composition may be continuously exposed to radiation throughout the entire hardening process (e.g., about 2 seconds to about 60 seconds). It is also possible to expose the composition to a single dose of radiation, and then remove the radiation source, thereby allowing polymerization to occur. In some cases materials can be subjected to light sources that ramp from low intensity to high intensity. Where dual exposures are employed, the intensity of each dosage may be the same or different. Similarly, the total energy of each exposure may be the same or different.

The multifunctional polymerizable ionic liquid or compositions comprising such may be chemically hardenable, i.e., the compositions contain a chemical initiator (i.e., initiator system) that can polymerize, cure, or otherwise harden the composition without dependence on irradiation with actinic radiation. Such chemically hardenable (e.g., polymerizable or curable) composition are sometimes referred to as "self-cure" compositions and may include redox cure systems, thermally curing system and combinations thereof. Further, the polymerizable composition may comprise a combination of different initiators, at least one of which is suitable for initiating free radical polymerization.

The chemically hardenable compositions may include redox cure systems that include a polymerizable component (e.g., an ethylenically unsaturated polymerizable component) and redox agents that include an oxidizing agent and a reducing agent.

The reducing and oxidizing agents react with or otherwise cooperate with one another to produce free-radicals capable of initiating polymerization of the resin system (e.g., the ethylenically unsaturated component). This type of cure is a dark reaction, that is, it is not dependent on the presence of light and can proceed in the absence of light. The reducing and oxidizing agents are preferably sufficiently shelf-stable and free of undesirable colorization to permit their storage and use under typical conditions.

Useful reducing agents include ascorbic acid, ascorbic acid derivatives, and metal complexed ascorbic acid compounds as described in U.S. Pat. No. 5,501,727 (Wang et al.); amines, especially tertiary amines, such as 4-tert-butyl dimethylaniline; aromatic sulfinic salts, such as p-toluenesulfinic salts and benzenesulfinic salts; thioureas, such as 1-ethyl-2-thiourea, tetraethyl thiourea, tetramethyl thiourea, 1,1-dibutyl thiourea, and 1,3-dibutyl thiourea; and mixtures thereof. Other secondary reducing agents may include cobalt (II) chloride, ferrous chloride, ferrous sulfate, hydrazine, hydroxylamine (depending on the choice of oxidizing agent), salts of a dithionite or sulfite anion, and mixtures thereof. Preferably, the reducing agent is an amine.

Suitable oxidizing agents will also be familiar to those skilled in the art, and include but are not limited to persulfuric acid and salts thereof, such as sodium, potassium, ammonium, cesium, and alkyl ammonium salts. Additional oxidizing agents include peroxides such as benzoyl peroxides, hydroperoxides such as cumyl hydroperoxide, t-butyl hydroperoxide, and amyl hydroperoxide, as well as salts of transition metals such as cobalt (III) chloride and ferric chloride, cerium (IV) sulfate, perboric acid and salts thereof, permanganic acid and salts thereof, perphosphoric acid and salts thereof, and mixtures thereof.

It may be desirable to use more than one oxidizing agent or more than one reducing agent. Small quantities of transition metal compounds may also be added to accelerate the rate of redox cure. The reducing or oxidizing agents can be microencapsulated as described in U.S. Pat. No. 5,154,762 (Mitra et al.). This will generally enhance shelf stability of the polymerizable composition, and if necessary permit packaging the reducing and oxidizing agents together. For example, through appropriate selection of an encapsulant, the oxidizing and reducing agents can be combined with an acid-functional component and optional filler and kept in a storage-stable state.

Compositions of this invention can also be cured with a thermally or heat activated free radical initiator. Typical thermal initiators include peroxides such as benzoyl peroxide and azo compounds such as azoisobutyronitrile.

The optical films having an antistatic coating as described herein are static dissipative and will dissipate 90% of a 5 kilovolt charge applied to the front surface in less then 10 seconds and preferably less then 5 second. Column 13 of U.S. Pat. No. 6,740,413 describes test methods for static dissipation and surface resistivity. The specific procedures used here are described in the experimental section. In some embodiments, the static decay time is no greater than 2 second. Some preferred antistatic agents provide static decay times of no greater than 0.5, 0.4, 0.3, 0.2, or 0.1 seconds.

Some advantages include that the antistatic layers disclosed herein (1) adhere well to a variety of optical films; (2) impart good antistatic properties to the resultant optical device; (3) can be durable so as to withstand handling and manipulation as the optical device is used, e.g., to manufacture a display device; and (4) are clear and colorless, making them well suited for various light management purposes as they can be used as is or have additional agents imparted therein to provide color selection, haze, or other desired effect.

A preferred monofunctional (e.g. mono(methacrylate) polymerizable ionic liquid to be used in combination with the polymerizable ionic liquid having a multifunctional cation has the formula $$(R^1)_{a-b}G^+[(CH_2)_q DR^2]_b X^-$$

wherein X, R¹, and R² are the same as previously described;
G is nitrogen, sulfur or phosphorous;
a is 3 where G is sulfur and a is 4 where G is nitrogen or phosphorous then;
b is 1;
q is an integer from 1 to 4; and
D is oxygen, sulfur, or NR wherein R is H or a lower alkyl of 1 to 4 carbon atoms.

In some embodiments, in which G is included in the cycle, the onium salt has one of the following formulas:

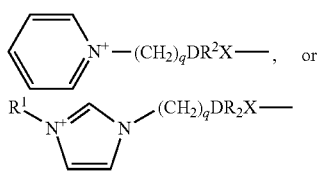

In some embodiments, G is a nitrogen atom of an ammonium cation. In some embodiments, D is oxygen. Further, in some embodiments R¹ is a lower alkyl of 1 to 4 carbon atoms.

Illustrative examples of anions useful herein include the same anions as previously described.

Fluorochemical anions can be favored for antistatic coating. Thus, in some embodiments, the anion is a fluorochemical anion. In some embodiments, the anion of the polymerizable ionic liquid having a multifunctional cation, as described herein, is a fluorochemical anion. In other embodiments, the monofunctional polymerizable ionic liquid, that is employed in combination with the polymerizable ionic liquid having a multifunctional cation, is a fluorochemical anion. Some illustrative examples include —C(SO$_2$CF$_3$)$_3$, —O$_3$SCF$_3$, —O$_3$SC$_4$F$_9$, and —N(SO$_2$CF$_3$)$_2$. Due to availability and cost the following are often preferred: —O$_3$SCF$_3$, —O$_3$SC$_4$F$_9$, and —N(SO$_2$CF$_3$)$_2$.

Representative examples of weakly coordinating fluoroorganic anions useful herein include such anions as fluorinated arylsulfonates, perfluoroalkanesulfonates, cyanoperfluoroalkanesulfonylamides, bis(cyano)perfluoroalkanesulfonylmethides, bis(perfluoroalkanesulfonyl)imides, cyano-bis-(perfluoroalkanesulfonyl)methides, bis(perfluoroalkanesulfonyl)methides, and tris(perfluoroalkanesulfonyl)methides; and the like.

Examples of suitable weakly coordinating fluoroorganic anions include the following:

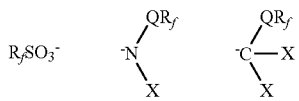

wherein each R$_f$ is independently a fluorinated alkyl or aryl group that may be cyclic or acyclic, saturated or unsaturated, and may optionally contain catenated ("in-chain") or terminal heteroatoms such as N, O, and S (e.g., —SF$_4$— or —SF$_5$). Q is independently an SO$_2$ or a CO linking group and X is selected from the group QR$_f$, CN, halogen, H, alkyl, aryl, Q-alkyl, and Q-aryl. Any two contiguous R$_f$ groups may be linked to form a ring. Preferably, R$_f$ is a perfluoroalkyl group, Q is SO$_2$ and each X is QR$_f$.

If fluoroorganic anions are used, they can be either fully fluorinated, that is perfluorinated, or partially fluorinated (within the organic portion thereof) as desired. Fluoroorganic anions include those that comprise at least one highly fluorinated alkanesulfonyl group, that is, a perfluoroalkanesulfonyl group or a partially fluorinated alkanesulfonyl group wherein all non-fluorine carbon-bonded substituents are bonded to carbon atoms other than the carbon atom that is directly bonded to the sulfonyl group (preferably, all non-fluorine carbon-bonded substituents are bonded to carbon atoms that are more than two carbon atoms away from the sulfonyl group).

The fluoroorganic anion may be at least about 80% fluorinated (that is, at least about 80% of the carbon-bonded substituents of the anion are fluorine atoms). The anion may be perfluorinated (that is, fully fluorinated, where all of the carbon-bonded substituents are fluorine atoms). The anions, including the preferred perfluorinated anions, can contain one or more catenated (that is, in-chain) or terminal heteroatoms such as, for example, nitrogen, oxygen, or sulfur (e.g., —SF$_4$— or —SF$_5$).

Organic and fluoroorganic anions include perfluoroalkanesulfonates, fluoroorganic anions with two or three sulfonate groups, bis(perfluoroalkanesulfonyl)imides, and tris(perfluoroalkanesulfonyl)methides; perfluoroalkanesulfonates and bis(perfluoroalkanesulfonyl)imides). Preferred anions for some embodiments are perfluorinated where all X's are QR$_f$, and all Q's are SO$_2$, more preferably the anion is a perfluoroalkanesulfonate or a bis(perfluoroalkanesulfonyl)imide, most preferably the anion is a bis(perfluoroalkanesulfonyl) imide.

The fluoroorganic ions can provide greater solubility and compatibility of the onium salt with the non-onium polymerizable monomers, oligomers, or polymers. This is important in providing a layer with good clarity, and good ion mobility which can improve the antistatic performance of the layer. Preferred anions include —C(SO$_2$CF$_3$)$_3$, —O$_3$SCF$_3$, —O$_3$SC$_4$F$_9$, and —N(SO$_2$CF$_3$)$_2$. More preferred anions, due to availability and cost are —O$_3$SCF$_3$, —O$_3$SC$_4$F$_9$, and —N(SO$_2$CF$_3$)$_2$, while the most preferred anion is —N(SO$_2$CF$_3$)$_2$.

Illustrative examples of polymerizable silicone monomers, oligomers, and polymers can be obtained from Degussa under the TEGO® Rad group of products. Especially useful polymerizable silicones are acrylate functional silicone polyethers, like TEGO™ Rad 2250.

The antistatic layers may also be made using polymerizable perfluoropolyether moiety-containing monomers, oligomers, or polymers, either instead of or in addition to the polymerizable silicone monomers, oligomers, and polymers discussed above. U.S. Patent Appln. Publn. 2006/0216500A1 (Klun et al.) discloses the synthesis of perfluoropolyether moiety containing urethane acrylates useful herein. U.S. Patent Appln. Publn. No. 2008-0124555 (Klun et al.) discloses perfluoropolyether moiety containing urethane acrylates containing poly(ethylene oxide) moieties case that would be useful herein. PCT WO2009/029438 (Pokorny et al.) discloses curable silicones with perfluoropolyether moiety containing urethane acrylates that would be useful herein.

As will be known to those skilled in the art, surface matte coatings are often useful in optical films and it may be desired to impart such matte properties to antistatic coatings of the invention. The increased haze and reduced clarity from a matte coating helps provide a more uniform display, and hide optical defects from the underlying film stack and backlight, especially in liquid crystal displays (LCDs). Various means are available to provide a matte coating and are useful with the present invention.

A multiphase coating can have a matte surface structure generated from immiscible materials incorporated in the coating at the surface or within the bulk of the coating, e.g., entrainment of particles such as polymethyl methacrylate beads in the coating. In some embodiments, particles with different refractive index from the bulk of the coating can be used to impart desired haze properties without necessarily yielding a matte surface. Though useful particles can be of any shape, typically preferred particle shapes are often in the form of spherical or oblong beads. Preferable particle sizes are generally about 0.1 microns to about 20 microns in average diameter. Particles can be made from any material that is compatible with the coating. Some illustrative examples of suitable materials for particles include polymethyl methacrylate, polybutyl methacrylate, polystyrene, polyurethane, polyamide, polysilicone, and silica. Useful particles can be obtained from Ganz Chemical, Sekisui Plastics Co., Ltd., and Soken Chemical & Engineering Co., Ltd, all of Japan.

Particularly when the polymerizable composition is employed for uses wherein transparency is important (such as an antistatic layer for use with optical films), the polymerizable ionic liquid(s) and optional polymerizable silicone content, as well as other components, if any, should be compatible in that they will mix and polymerize to form transparent films.

In addition to the polymerizable ionic liquid(s) and polymerizable silicone components described above, antistatic layers of the invention can be made from curable compositions further comprising polymerizable non-silicone monomers, oligomers, or polymers. Such materials might be used to modify properties of the resultant layer, e.g., adhesion to the optical film, flexibility, or other mechanical properties, optical properties, e.g., its haze, clarity, etc.; reduce cost, etc.

Some illustrative examples of polymerizable (i.e. non-silicon, non-onium) monomers, oligomers, or polymers useful herein include, for example, poly(meth)acryl monomers selected from the group consisting of (a) mono(methacryl) containing compounds such as phenoxyethyl acrylate, ethoxylated phenoxyethyl acrylate, 2-ethoxyethoxyethyl acrylate, ethoxylated tetrahydrofurfural acrylate, and caprolactone acrylate, (b) di(meth)acryl containing compounds such as 1,3-butylene glycol diacrylate, 1,4-butanediol diacrylate, 1,6-hexanediol diacrylate, 1,6-hexanediol monoacrylate monomethacrylate, ethylene glycol diacrylate, alkoxylated aliphatic diacrylate, alkoxylated cyclohexane dimethanol diacrylate, alkoxylated hexanediol diacrylate, alkoxylated neopentyl glycol diacrylate, caprolactone modified neopentylglycol hydroxypivalate diacrylate, caprolactone modified neopentylglycol hydroxypivalate diacrylate, cyclohexanedimethanol diacrylate, diethylene glycol diacrylate, dipropylene glycol diacrylate, ethoxylated (10) bisphenol A diacrylate, ethoxylated (3) bisphenol A diacrylate, ethoxylated (30) bisphenol A diacrylate, ethoxylated (4) bisphenol A diacrylate, hydroxypivalaldehyde modified trimethylolpropane diacrylate, neopentyl glycol diacrylate, polyethylene glycol (200) diacrylate, polyethylene glycol (400) diacrylate, polyethylene glycol (600) diacrylate, propoxylated neopentyl glycol diacrylate, tetraethylene glycol diacrylate, tricyclodecanedimethanol diacrylate, triethylene glycol diacrylate, tripropylene glycol diacrylate; (c) tri(meth)acryl containing compounds such as glycerol triacrylate, trimethylolpropane triacrylate, pentaerthyritol triacrylate, ethoxylated triacrylates (e.g., ethoxylated (3) trimethylolpropane triacrylate, ethoxylated (6) trimethylolpropane triacrylate, ethoxylated (9) trimethylolpropane triacrylate, ethoxylated (20) trimethylolpropane triacrylate), propoxylated triacrylates (e.g., propoxylated (3) glyceryl triacrylate, propoxylated (5.5) glyceryl triacrylate, propoxylated (3) trimethylolpropane triacrylate, propoxylated (6) trimethylolpropane triacrylate), trimethylolpropane triacrylate, tris(2-hydroxyethyl)isocyanurate triacrylate; (d) higher functionality (meth)acryl containing compounds such as pentaerythritol tetraacrylate, ditrimethylolpropane tetraacrylate, dipentaerythritol pentaacrylate, ethoxylated (4) pentaerythritol tetraacrylate, caprolactone modified dipentaerythritol hexaacrylate; (e) oligomeric (meth)acryl compounds such as, for example, urethane acrylates, polyester acrylates, epoxy acrylates; polyacrylamide analogues of the foregoing; and combinations thereof. Such compounds are widely available from vendors such as, for example, Sartomer Company of Exton, Pennsylvania; UCB Chemicals Corporation of Smyrna, Ga.; Cytec Corporation, Cognis, and Aldrich Chemical Company of Milwaukee, Wis. Additional useful (meth)acrylate materials include hydantoin moiety-containing poly(meth)acrylates, for example, as described in U.S. Pat. No. 4,262,072 (Wendling et al.).

Optical Films

Typically, the optical film in a device of the invention will be selected from the group consisting of reflective polarizers (e.g., so-called multilayer optical films or "MOFs" having regularly repeating layers of alternating refractive indices), brightness enhancement films, and diffuse reflecting polarizer films (sometimes referred to as "DRPFs" having multiphase structures with domains of alternating refractive indices.). One illustrative example of a reflective polarizer is VIKUITI™ Dual Brightness Enhancement Film II (DBEF-II), commercially available from 3M, and described in U.S. Pat. No. 7,345,137 (Hebrink et al.). Suitable prismatic brightness enhancement films (sometimes referred to as "BEFs"), also commercially available from 3M, are described in, e.g., U.S. Pat. No. 5,771,328 (Wortman et al.), U.S. Pat. No. 6,280,063 (Fong), and U.S. Pat. No. 6,354,709 (Campbell et al.) and U.S. Patent Appln. Publn. No. 2009/0017256 (Hunt et al.). Illustrative examples of diffuse reflecting polarizer films that can be used herein include those disclosed in U.S. Pat. No. 5,825,543 (Ouderkirk et al.). Illustrative examples of commercially available optical films suitable for use herein include VIKUITI™ Dual Brightness Enhanced Film (DBEF), VIKUITI™ Brightness Enhanced Film (BEF), VIKUITI™ Diffuse Reflective Polarizer Film (DRPF), VIKUITI™ Enhanced Specular Reflector (ESR), and VIKUITI™ Advanced Polarizing Film (APF), all available from 3M Company.

As described in U.S. Pat. No. 5,175,030 (Lu et al.), and U.S. Pat. No. 5,183,597 (Lu), a microstructure-bearing article (e.g. brightness enhancing film) can be prepared by a method including the steps of (a) preparing a polymerizable composition; (b) depositing the polymerizable composition onto a master negative microstructured molding surface in an amount barely sufficient to fill the cavities of the master; (c) filling the cavities by moving a bead of the polymerizable composition between a preformed base (such as a PET film) and the master, at least one of which is flexible; and (d) curing the composition to yield an array of microstructured optical elements on the base. The master can be metallic, such as nickel, nickel-plated copper or brass, or can be a thermoplastic material that is stable under the polymerization conditions, and that preferably has a surface energy that allows clean removal of the polymerized material from the master.

Useful base materials include, for example, styrene-acrylonitrile, cellulose acetate butyrate, cellulose acetate propionate, cellulose triacetate, polyether sulfone, polymethyl methacrylate, polyurethane, polyester, polycarbonate, polyvinyl chloride, polystyrene, polyethylene naphthalate, copolymers or blends based on naphthalene dicarboxylic acids, polycyclo-olefins, polyimides, and glass. Optionally, the base material can contain mixtures or combinations of these materials. Further, the base may be multi-layered or may contain a dispersed component suspended or dispersed in a continuous phase.

For some microstructure-bearing products such as brightness enhancement films, examples of preferred base materials include polyethylene terephthalate (PET) and polycarbonate. Examples of useful PET films include photograde polyethylene terephthalate and MELINEX™ PET available from DuPont Films of Wilmington, Del.

Some base materials can be optically active, and can act as polarizing materials. Polarization of light through a film can be accomplished, for example, by the inclusion of dichroic polarizers in a film material that selectively absorbs passing light. Light polarization can also be achieved by including inorganic materials such as aligned mica chips or by a discontinuous phase dispersed within a continuous film, such as droplets of light modulating liquid crystals dispersed within a continuous film. As an alternative, a polarizing film can be prepared from microfine layers of different materials. The materials within the film can be aligned into a polarizing orientation, for example, by employing methods such as stretching the film, applying electric or magnetic fields, and coating techniques.

Examples of polarizing films include those described in U.S. Pat. No. 5,825,543 (Ouderkirk et al.) and U.S. Pat. No. 5,783,120 (Ouderkirk et al.). The use of these polarizer films in combination with a brightness enhancement film has been described in U.S. Pat. No. 6,111,696 (Allen et al.). Another example of a polarizing film that can be used as a base are those films described in U.S. Pat. No. 5,882,774 (Jonza et al.).

One or more of the surfaces of the base film material can optionally be primed or otherwise be treated to promote adhesion of the optical layer to the base. Primers particularly suitable for polyester base film layers include sulfopolyester primers, such as described in U.S. Pat. No. 5,427,835 (Morrison et al.). The thickness of the primer layer is typically at least about 20 nm and generally no greater than about 300 nm to about 400 nm.

The optical elements can have any of a number of useful patterns. These include regular or irregular prismatic patterns, which can be an annular prismatic pattern, a cube-corner pattern or any other lenticular microstructure. A useful microstructure is a regular prismatic pattern that can act as a totally internal reflecting film for use as a brightness enhancement film. Another useful microstructure is a corner-cube prismatic pattern that can act as a retroreflecting film or element for use as reflecting film. Another useful microstructure is a prismatic pattern that can act as an optical turning film or element for use in an optical display.

One preferred optical film having a polymerized microstructured surface is a brightness enhancing film. Brightness enhancing films generally enhance on-axis luminance (referred herein as "brightness") of a lighting device. The microstructured topography can be a plurality of prisms on the film surface such that the films can be used to redirect light through reflection and refraction. The height of the prisms typically ranges from about 1 to about 75 microns. When used in an optical display such as that found in laptop computers, watches, etc., the microstructured optical film can increase brightness of an optical display by limiting light escaping from the display to within a pair of planes disposed at desired angles from a normal axis running through the optical display. As a result, light that would exit the display outside of the allowable range is reflected back into the display where a portion of it can be "recycled" and returned back to the microstructured film at an angle that allows it to escape from the display. The recycling is useful because it can reduce power consumption needed to provide a display with a desired level of brightness.

The microstructured optical elements of a brightness enhancing film generally comprise a plurality of parallel longitudinal ridges extending along a length or width of the film. These ridges can be formed from a plurality of prism apexes. Each prism has a first facet and a second facet. The prisms are formed on base that has a first surface on which the prisms are formed and a second surface that is substantially flat or planar and opposite first surface. By right prisms it is meant that the apex angle is typically about 90°. However, this angle can range from about 70° to about 120° and may range from about 80° to about 100°. These apexes can be sharp, rounded or flattened or truncated. For example, the ridges can be rounded to a radius in a range of about 4 to about 7 to about 15 micrometers. The spacing between prism peaks (or pitch) can be about 5 to about 300 microns. The prisms can be arranged in various patterns such as described in U.S. Pat. No. 7,074,463 (Jones et al.).

In optical devices of the invention using thin brightness enhancing films, the pitch is preferably about 10 to about 36 microns, and more preferably about 17 to about 24 microns. This corresponds to prism heights of preferably about 5 to about 18 microns, and more preferably about 9 to about 12 microns. The prism facets need not be identical, and the prisms may be tilted with respect to each other. The relationship between the total thickness of the optical article, and the height of the prisms, may vary. However, it is typically desirable to use relatively thinner optical layers with well-defined prism facets. For thin brightness enhancing films on substrates with thicknesses close to about 1 mil (about 20 to about 35 microns), a typical ratio of prism height to total thickness is generally between about 0.2 and about 0.4. In other embodiments, thicker BEF materials will be used, BEF materials a 50 micron pitch and 25 micron thickness.

As will be understood by those skilled in the art, optical devices of the invention may be made using other kinds of optical layers or other embodiments of MOF, BEF, or DRPF materials than those illustrative examples discussed above.

Outer layer antistatic coatings on brightness enhancement films should impart minimal absorbance and color, so as not to interfere with brightness enhancement properties of the films. The coatings may increase haze and reduce clarity to provide a uniform display, and hide optical defects from the underlying film stack and backlight. They should provide reasonable durability.

In perhaps the simplest embodiments, devices of the invention will comprise an optical layer with antistatic layer as described herein on one surface thereof. In some embodiments, the optical device might comprise antistatic layers of the invention on each surface of the optical layer, e.g., DBEF-II, wherein the antistatic layers may be the same or may be optimized independently, e.g., PMMA beads in one antistatic layer but not the other, etc.

EXAMPLES

The invention will be explained with reference to the following illustrative examples. All amounts are expressed in wt. % unless otherwise indicated.

Test Methods

Average static decay was determined using the following method. Sheets of test materials were cut into 12 cm by 15 cm samples and conditioned at relative humidity (RH) of about 50% for at least 12 hours. The materials were tested at temperatures that ranged from 22-25° C. The static charge dissipation time was measured according to MIL-STD 3010, Method 4046, formerly known as the Federal Test Method Standard 10113, Method 4046, "Antistatic Properties of Materials", using an ETS Model 406D Static Decay Test Unit (manufactured by Electro-Tech Systems, Inc., Glenside, Pa.). This apparatus induces an initial static charge (Average Induced Electrostatic Charge) on the surface of the flat test material by using high voltage (5000 volts), and a field meter allows observation of the decay time of the surface voltage from 5000 volts (or whatever the induced electrostatic charge was) to 10 percent of the initial induced charge. This is the static charge dissipation time. The lower the static charge dissipation time, the better the antistatic properties are of the test material. All reported values of the static charge dissipation times in this invention are averages (Average Static Decay Rate) over at least 3 separate determinations. Values reported as >60 seconds indicate that the sample tested has an initial static charge that cannot be removed by surface conduction and is not antistatic. When the sample tested did not accept a charge of about 3000 volts or more, it was not considered to have charged sufficiently to be antistatic.

Materials

DBEF Film (Optical Layer): In each example, VIKUITI™ Dual Brightness Enhancement Film II (or DBEF II) from 3M was used as the optical film. Such films can be produced as follows:

A multilayer reflective polarizer film was constructed with first optical layers created from a polyethylene naphthalate and second optical layers created from co(polyethylene naphthalate) and skin layers or non-optical layers created from a cycloaliphatic polyester/polycarbonate blend commercially available from Eastman Chemical Company under the tradename "VM365" and additionally blended with Styrene-Acrylate copolymer "NAS30" available from NOVA Chemicals.

The copolyethylene-hexamethylene naphthalate polymer (CoPEN5050HH) used to form the first optical layers is synthesized in a batch reactor with the following raw material charge: dimethyl 2,6-naphthalenedicarboxylate (80.9 kg), dimethyl terephthalate (64.1 kg), 1,6-hexane diol (15.45 kg), ethylene glycol (75.4 kg), trimethylol propane (2 kg), cobalt (II) acetate (25 g), zinc acetate (40 g), and antimony (III) acetate (60 g). The mixture was heated to a temperature of 254° C. at a pressure of two atmospheres ($2 \times 10^5$ N/m$^2$) and the mixture was allowed to react while removing the methanol reaction product. After completing the reaction and removing the methanol (approximately 42.4 kg) the reaction vessel was charged with triethyl phosphonoacetate (55 g) and the pressure was reduced to one torr (263 N/m$^2$) while heating to 290° C. The condensation by-product, ethylene glycol, was continuously removed until a polymer with intrinsic viscosity 0.55 dl/g as measured in a 60/40 weight percent mixture of phenol and o-dichlorobenzene is produced. The CoPEN5050HH polymer produced by this method had a glass transition temperature ($T_g$) of 85° C. as measured by differential scanning calorimetry at a temperature ramp rate of 20° C. per minute. The CoPEN5050HH polymer had a refractive index of 1.601 at 632 nm.

The above described PEN and CoPEN5050HH were coextruded through a multilayer melt manifold to create a multilayer optical film with 275 alternating first and second optical layers. This 275 layer multi-layer stack was divided into 3 parts and stacked to form 825 layers. The PEN layers were the first optical layers and the CoPEN5050HH layers were the second optical layers. In addition to the first and second optical layers, two sets of skin layers were coextruded on the outer side of the optical layers through additional melt ports. VM365 blended with 22 wt % NAs30 was used to form the external set of skin layers. The construction was, therefore, in order of layers: VM365/NAS30 blend outer skin layer, 825 alternating layers of optical layers one and two, VM365/NAS30 blend outer skin layer.

The multilayer extruded film was cast onto a chill roll at 5 meters per minute (15 feet per minute) and heated in an oven at 150° C. (302° F.) for 30 seconds, and then uniaxially oriented at a 5.5:1 draw ratio. A reflective polarizer film of approximately 150 microns (8 mils) thickness was produced.

This multilayer film was measured to have a haze level of 42% as measured with a Gardner haze meter. This multilayer film when exposed to the thermal shock test (warp test) had an acceptable level of warp after 100 hrs of thermal cycling from −35° C. to 85° C.

Synthesis of Polymerizable Ionic Liquids Having Multifunctional Cation

Preparation of PIL A

Step 1: Preparation of a Bis Hydroxyethylated Imidazolium Salt.

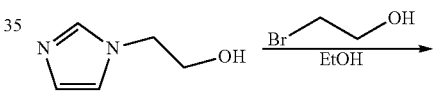

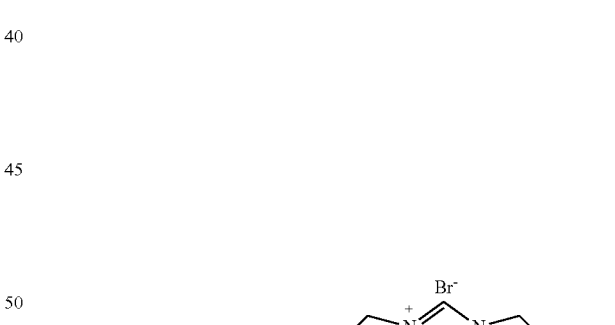

A solution of 1-(2-hydroxyethyl)imidazole (25.0 g, 0.22 mol, available from Aldrich) and 2-bromoethanol (27.9 g, 0.22 mol, available from Aldrich) in ethanol (100 mL) was heated at reflux for 36 hours, then cooled to room temperature and the ethanol removed at reduced pressure. The remaining oil was extracted with 4 100 mL portions of methylene chloride, then concentrated under reduced pressure to leave the bis hydroxyethylated imidazolium salt as an orange oil (50.1 g). NMR analysis of the oil confirmed that the desired product had been formed.

Step 1: Preparation of the Bis Methacrylate Ionic Liquid

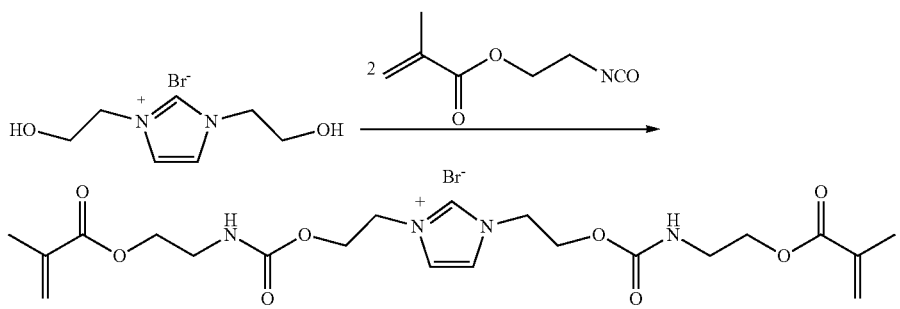

A mixture of the the bis hydroxyethylated imidazolium salt from Step 1 (4.40 g, 18.6 mmol), 2-isocyanatoethyl methacrylate (5.75 g, 37.1 mmol, available from Aldrich), and 1 drop (about 20 mg) of dibutyltin dilaurate (available from Aldrich) in methylene chloride (50 mL) was stirred at room temperature for 4 days. At this time the initially insoluble salt had dissolved and analysis of the reaction mixture by infrared spectroscopy showed that the initially present isocyanate absorption at 2275 cm$^{-1}$ was gone. NMR analysis of a portion of the reaction product from which the methylene chloride had been removed at reduced pressure confirmed that the desired bis methacrylate had been formed. The bis methacrylate was kept in the methylene chloride solution and used as such.

Preparation of PIL B

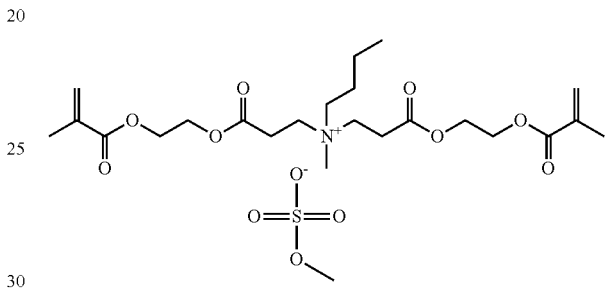

A mixture of n-butylamine (0.993 g, 14 mmol, Aldrich) and methacryloxyethyl acrylate (5.00 g, 27 mmol, prepared according to Klee, J. E., et. al., *Macromol. Chem. Phys.*, 200, 1999, 517) was stirred at room temperature for 24 hours. The intermediate product was a colorless liquid.

Dimethyl sulfate (0.57 g, 4.5 mmol) was added to the intermediate product from above (2.00 g, 4.5 mmol) dropwise over 10 minutes. The mixture was stirred for 17 hours to give the final PIL product as a thick liquid.

Preparation of PIL-C ("POS-2")

Polymerizable Onium Salt 2 (POS-2): Represented by the Following Formula:

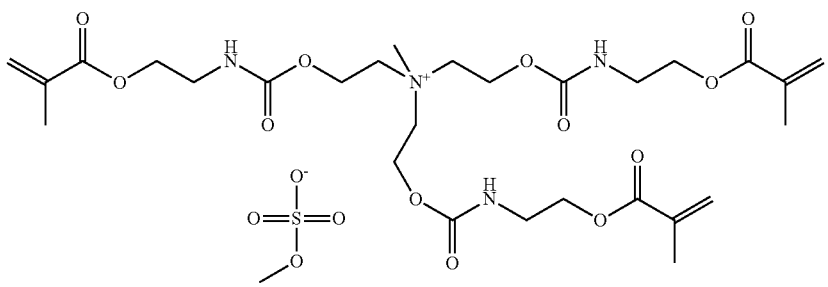

To a solution of tris-(2-hydroxyethyl)methylammonium methylsulfate (11.58 g, 0.04 mol, available from BASF), isocyanatoethyl methacrylate (19.58 g, 0.12 mol), and 2,6-di-tert-butyl-4-methylphenol (BHT, 0.020 g, available from Aldrich) in methylene chloride (50 mL) in a flask fitted with a drying tube and a magnetic stirrer was added a drop of dibutyltin dilaurate. The solution was cooled in an ice bath and stirred for 3 hours, then allowed to warm to room temperature and stirring was continued for another 36 hours. Progress of the reaction was monitored by infrared spectroscopy, observing the disappearance of the isocyanate absorbtion. When reaction was complete the solvent was removed at reduced pressure yielding a very viscous liquid.

Preparation of PIL D trade designation "HQ-115", 6.82 g of 80% solids solution in water (0.0190 mol) was added over 10 seconds, with precipitation of a whitish solid, followed by addition of 0.78 g of water. The flask was removed from the flask and 50 g of methylene chloride was added to the reaction with stirring. The reaction was allowed to separate in a separatory funnel, and the lower organic layer was washed with 15.1 g water. The organic layer was again separated, dried over anhydrous magnesium sulfate, treated with 2 mg BHT, and concentrated under air at a pressure of 380 mm at 53° C. to yield 13.2 g of a clear thick oil.

Alternative Preparation of PIL-E

To a solution of tris-(2-hydroxyethyl)methylammonium methylsulfate (50.0 g, 0.182 mol, in 37.5 g water in a 250 mL flask in a 50 degree C. oil bath, was added lithium

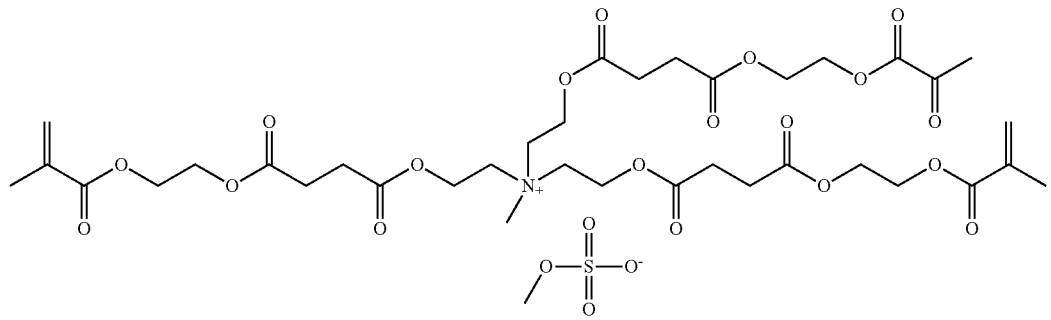

To a stirred, ice cooled solution of tris-(2-hydroxyethyl)methylammonium methylsulfate (17.38 g, 0.06 mol), mono-2-(methacryloyloxy)ethyl succinate (41.42 g, 0.18 mol, available from Aldrich), and 4-dimethylaminopyridine (1.098 g, 0.009 mol, available from Aldrich) in ethyl acetate (150 mL) was added dropwise over a 2 hour period a solution of 1,3-dicyclohexylcarbodiimide (DCC, 37.1 g, 0.18 mol, available from Aldrich) in ethyl acetate (150 mL). After the DCC solution was added, the temperature of the reaction mixture was allowed to rise gradually to room temperature, and then the reaction was stirred for 14 hours. Then 0.5 g of deionized water and 2.0 g of silica gel were added into the flask and the reaction mixture stirred for 1 hour. The mixture was then filtered and solvent removed from the filtrate at reduced pressure to yield a very viscous liquid product having a slight yellow color.

Preparation of PIL-E bis(trifluoromethanesulfonyl)imide (65.18 g of 80% solids solution in water (0.182 mol) with stirring over 20 seconds, followed by 6.26 g water. After 3 min of stirring the reaction was concentrated on a rotary evaporator in a bath at up to 100° C. to provide 101.75 g of

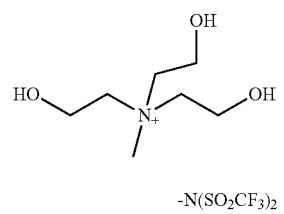

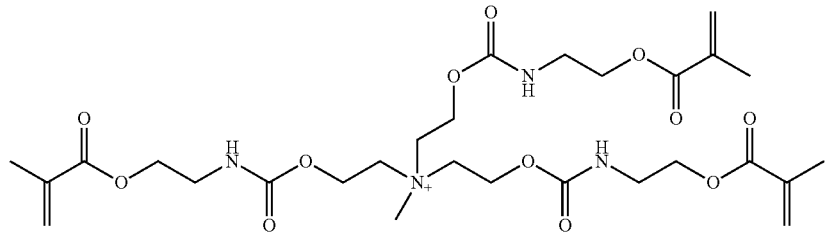

To PIL-C (14.09 g, 0.0190 mol) was added 14.09 g of water in a 250 mL roundbottom flask, which was heated under air in a 55° C. bath. Then lithium bis(trifluoromethanesulfonyl) imide, Li$^+$—N(SO$_2$CF$_3$)$_2$ from 3M Company, under the and Li+ —OSO$_3$CH$_3$ as a clear liquid with a dispersed whitish solid. This material when homogeneous is 78.85% by weight of the quat salt.

To 50 g of the mixture from the previous reaction (0.0889 mol, 0.267 OH equivalents of $(HOCH_2CH_2)_3N(CH_3)+$ $-N(SO_2CF_3)_2)$ in a 2 necked 250 mL roundbottom equipped with overhead stirrer, was added 56.62 g methylene chloride. The flask was placed into a 40° C. oil bath under air, and one drop of dibutyltin dilaurate. Next isocyanatoethyl methacrylate (41.40 g, 0.267 mol) was added over 20 min. The reaction was monitored by FTIR for the disappearance of the isocyanate peak at 2275 cm$^{-1}$, and was judged to be complete after 7 hours of reaction. To the room temperature reaction was added 75 g of methylene chloride and 50 g of water with stirring. The reaction was allowed to separate in a reparatory funnel, and the lower organic layer was dried over anhydrous magnesium sulfate, treated with 12 mg of BHT and concentrated under air at a pressure of 380 mm at 53° C. for about 5 hours to yield 86.76 g of a clear thick oil.

Preparation of PIL-F

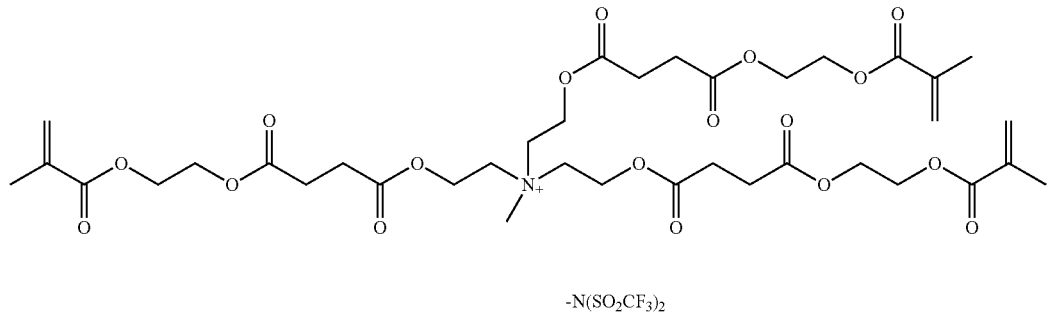 [SMILES: C=C(C)C(=O)OCCOC(=O)CCC(=O)OCC[N+](C)(CCOC(=O)CCC(=O)OCCOC(=O)C(=C)C)CCOC(=O)CCC(=O)OCCOC(=O)C(=C)C ; "-N(SO2CF3)2"]

$-N(SO_2CF_3)_2$

To PIL-D (15.74, 0.0173 mol) was added 15.74 g of water in a 125 mL roundbottom flask, which was heated under air in a 55° C. bath. The material was not very soluble in the water, and the reaction consisted of a cloudy upper phase and a liquid lower phase. Then lithium bis(trifluoromethanesulfonyl)imide, $Li^+{}^-N(SO_2CF_3)_2$, 6.20 g of 80% solids solution in water (0.0173 mol) was added over 10 seconds, with precipitation of a whitish solid, followed by addition of 5.84 g water. The reaction was stirred for 2 hours, then the temperature of the bath was dropped to 40° C. Next, 50 g of methylene chloride was added to the reaction with stirring for 30 min. The reaction was allowed to separate in a reparatory funnel, and the lower organic layer was washed with 25.0 g water. The organic layer was again separated, dried over anhydrous magnesium sulfate, and concentrated under air at a pressure of 280 mm at 53° C. to yield 16.12 g of a slightly yellow, clear oil.

Determination of Air to Nitrogen Curing Exotherm Ratio:

The photo polymerization behavior of monomers under N2 and air was examined using differential scanning photocalorimetry (photo DSC). The photo DSC was a TA instrument (New Castle, Del.) with DSC module 2920. The light source was a mercury/argon lamp with an Oriel PN 59480 425 nm long pass light filter. The light intensity was 3 mW/cm$^2$, measured using an International Light light meter Model IL 1400 equipped with a Model XRL, 340A detector. The photo curable samples contained 0.5% camphorquinone (Sigma-Aldrich), 1.0% ethyl 4-(N,N-dimethylamino)benzoate(Sigma-Aldrich) and 1.0% diphenyl iodonium hexafluorophosphate as the photoinitiator package. A 10 mg cured sample was used as a reference.

About 10 mg of the sample was weighed accurately for the testing with a Hermetic Pan (aluminum sample pan) as the sample holder. The samples were equilibrated at 37° C. for 5 minutes, and then the light aperture was opened to irradiate the sample. During irradiation the sample temperature was held at 37° C. The total irradiation time was 30 minutes. After 30 minutes, the aperture was closed and the sample maintained at 37° C. for another 5 minutes. The samples were tested under nitrogen and air atmosphere respectively.

The data was collected as heat output per unit weight (mW/g). The data was analyzed using TA Thermal Solutions Universal Analysis software.

Monomers were run once under nitrogen, then an identical sample was run under air. The DSC recorded the heat generation from the curing sample during exposure, and the area under the curve was integrated to give total Joules/gram. The heat generated when the sample was cured in air was divided by the heat generated when the sample was cured in nitrogen to give the curing ratio. A higher ratio represents less oxygen inhibition.

Testing Results for Photocuring a Multifunctional PIL and Triethylene Glycol Dimethacrylate (TEGDMA, Available from Aldrich) by Photo DSC

| sample | Curing ratio (air/N2) |
|---|---|
| PIL-C | 0.97 |
| TEGDMA | 0.36 |

Monofunctional Polymerizable Ionic Liquid Utilized in Combination with Multifunctional Polymerizable Ionic Liquid 1. Polymerizable Onium salt 1 (POS-1) $(CH_3)_3NCH_2CH_2OC(O)CH=CH_2{}^{+-}N(SO_2CF_3)_2$, -(Acryloyloxyethyl)-N,N,N-trimethylammonium bis(trifluoromethanesulfonyl)imide

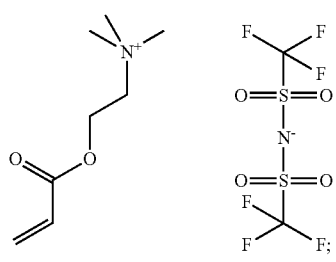

POS-1 was prepared as follows: To a tared 5 L, 3-necked round bottom flask equipped with overhead stirrer was charged 1486 g (79.1% solids in water, 6.069 mol) AGEFLEX™ FA1Q80MC*500 and the contents were heated to 40° C. To the flask was added, over about one minute, 2177.33 g (80% solids in water, 6.069 mol) HQ-115, followed by 597.6 g deionized water. After stirring for 1 hour, the reaction was transferred to a separatory funnel and the lower organic layer (2688.7 g) was returned to the reaction flask and washed with 1486 g deionized water at 40° C. for 30 min. The lower layer (2656.5 g) was again separated from the aqueous layer and place in a dry 5 L, 3-necked round bottom equipped with overhead stirrer and stillhead, and air bubbler. To the flask was added 2000 g acetone and the reaction was distilled at atmospheric pressure over 6 hours with an air sparge to azeotropically dry the product with a yield of 2591 g of a clear liquid, which slowly crystallizes to a solid;

2. Polymerizable Onium salt 1 ("POS-3") 3-butyl-1-[2-(2-methyl-acryloyloxy)-ethyl]-3H-imidazol-1-ium bromide

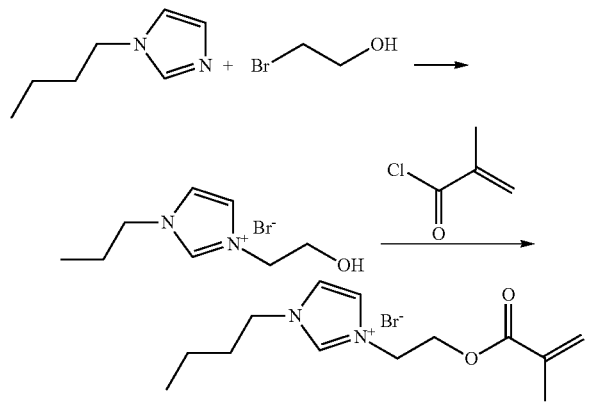

A) Synthesis of 3-Butyl-1-(2-hydroxy-ethyl)-3H-imidazol-1-ium bromide N-Butyl imidazole (freshly distilled. 37.2 g, 300 mmol) and 2-bromoethanol (freshly distilled. 37.5 g, 300 mmol) were mixed at room temperature to cause a slightly exothermic reaction. The mixture was heated at 50° C. for 90 hours. A very viscous liquid was obtained as product.

B) Synthesis of 3-butyl-1-[2-(2-methyl-acryloyloxy)-ethyl]-3H-imidazol-1-ium bromide To 3-butyl-1-(2-hydroxy-ethyl)-3H-imidazol-1-ium bromide (29.9 g, 120 mmol) was added 20 mg of BHT and 2-methacryloyl chloride (13.8 g, 132 mmol). The starting ionic liquid (IL) was insoluble in 2-methacryloyl chloride. The mixture was stirred at room temperature. The IL gradually dissolved and a uniform pink solution was obtained in about half an hour. Volatile side product and starting materials were removed under vacuum after 4 hours of reaction. A light brown liquid was obtained as product.

Examples 1 to 3

Three polymerizable clear coating formulations, having formulations as indicated, were prepared, coated on DBEF-II, dried, cured, and tested. These formulations all contained 85% methanol and 0.15% CIBA™ DAROCUR™ 4265 curing agent. Otherwise, they varied as shown in Table 1 below. Each formulation was mixed to ensure the soluble components were dissolved. Each formulation was further coated onto the back side of DBEF-II with a #16 wire wound Meyer rod, to give an average dry thickness of about 3 microns. Each coating was dried for 2 minutes in a batch oven at 140° F., and then UV cured in a nitrogen environment with two passes at 35 feet per minute, under a Fusion F600 Microwave driven medium pressure lamp using a D bulb, from Fusion UV Systems Inc. At a speed of 35 fpm, the UV energy emitted is as follows: UVA 460 mJ/cm$^2$, UVB 87 mJ/cm$^2$, UVC 12 mJ/cm$^2$, UVV 220 mJ/cm$^2$. All the coatings provided a smooth clear coating layer without interfering with the brightness enhancement properties of the DBEF-II film.

The formulations and static decay results are as shown in Table 1 wherein is seen the surprising and dramatic improvement of antistatic properties in a polymerizable clear coating from the combination of a polymerizable onium ionic liquid, and a polymerizable silicone.

TABLE 1

| Example | POS-1 (wt-% solids) | PIL-C (POS-2) (wt-% solids) | TEGO Rad 2250 polymerizable silicone (wt-% solids) | Avg Static Decay (Seconds) |
|---|---|---|---|---|
| Example 1 | 0 | 14.9 g (99%) | 0 | 4.8 |
| Example 2 | 0 | 14.7 g (97.8%) | 0.18 g (1.2) | 2.0 |
| Example 3 | 7.3 g (48.9%) | 7.3 g (48.9%) | 0.18 g (1.2) | 0.04 |

For Examples 4 and 5 the components as described in Table 2 were dissolved in 2.0 grams of methanol. Each formulation was coated onto PET film (available from Dupont under the trade designation "Melinex 618") with a #12 wire wound Meyer rod, to give an average dry thickness of about 10 microns. Each coating was dried for 5 minutes in a batch oven at 60° C., and then UV cured in a nitrogen environment with two passes at 30 feet per minute on a 6 inch UV curing process line equipped with a Fusion UV H bulb (on high power 100% UV that provides 58 mJ/cm$^2$ at the 30 feet per minute speed) from Fusion UV Systems Inc. All the cured coatings provided a non-tacky smooth clear coating layer.

The cured coatings were tested as previously described except that the cured coatings were tested immediately at ambient humidity, averaging 2 separate determinations.

TABLE 2

| Example | PIL - A (wt-% solids) | PIL-C (wt-% solids) | POS-3 (wt-% solids) | Darocur 1173 Photoinitiator | Avg Static Decay (Seconds) | Surface Resistance ohms/square |
|---|---|---|---|---|---|---|
| Example 4 | 0.0 g | 2.0 g (79.3%) | 0.50 g (19.8%) | 0.023 g (0.9%) | 0.19 | $1.70 \times 10^{11}$ |
| Example 5 | 3.0 g (91.7%) | 0.0 g | 0.25 g (7.6%) | 0.023 g (0.8%) | 0.02 | $2.60 \times 10^9$ |

Although the present invention has been fully described in connection with the preferred embodiments thereof with reference to the accompanying drawings, it is to be noted that various changes and modifications are apparent to those skilled in the art. Such changes and modifications are to be understood as included within the scope of the present invention.

The patents and patent applications cited herein are all incorporated by reference in their entirety.

What is claimed is:

1. A coating comprising a multifunctional polymerizable ionic liquid comprising an anion and a cationic group having at least two (meth)acrylate groups, each bonded to the cationic group via a divalent linking group wherein the linking group independently comprises one or more linkages selected from amide, urethane, urea, ether, or ester and the multifunctional polymerizable ionic liquid has an air to nitrogen curing exotherm ratio of at least 0.70; and a monofunctional polymerizable ionic liquid.

2. The coating of claim 1 wherein the multifunctional polymerizable ionic liquid has an air to nitrogen curing exotherm ratio of at least 0.90.

3. The coating of claim 1 wherein the cationic group is an onium salt selected from substituted imidazolium, substituted ammonium, substituted phosphonium.

4. The coating of claim 1 wherein the cationic group is substituted imidazolium.

5. The coating of claim 1 wherein the anion is a sulfonate.

6. The coating of claim 1 wherein the linking groups comprise a urethane linkage.

7. The coating of claim 1 wherein the multifunctional polymerizable ionic liquid has the formula

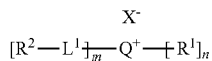

wherein:

Q is nitrogen or phosphorous;

$R^1$ is independently hydrogen, alkyl, aryl, alkaryl, or a combination thereof;

$R^2$ is independently a (meth)acrylate group;

$L^1$ is independently a linking group with the proviso that at least two of the linking groups independently comprise one or more linkages selected from amide, urethane, urea, ether, or ester;

m is an integer of 2 to 4;

n is an integer of 0 to 2;

and m+n=4;

X is an anion.

8. The coating of claim 1 wherein the multifunctional polymerizable ionic liquid has the formula

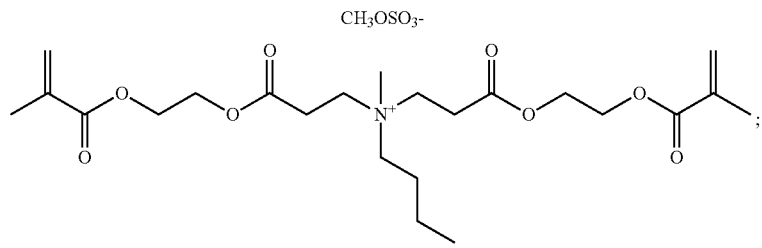

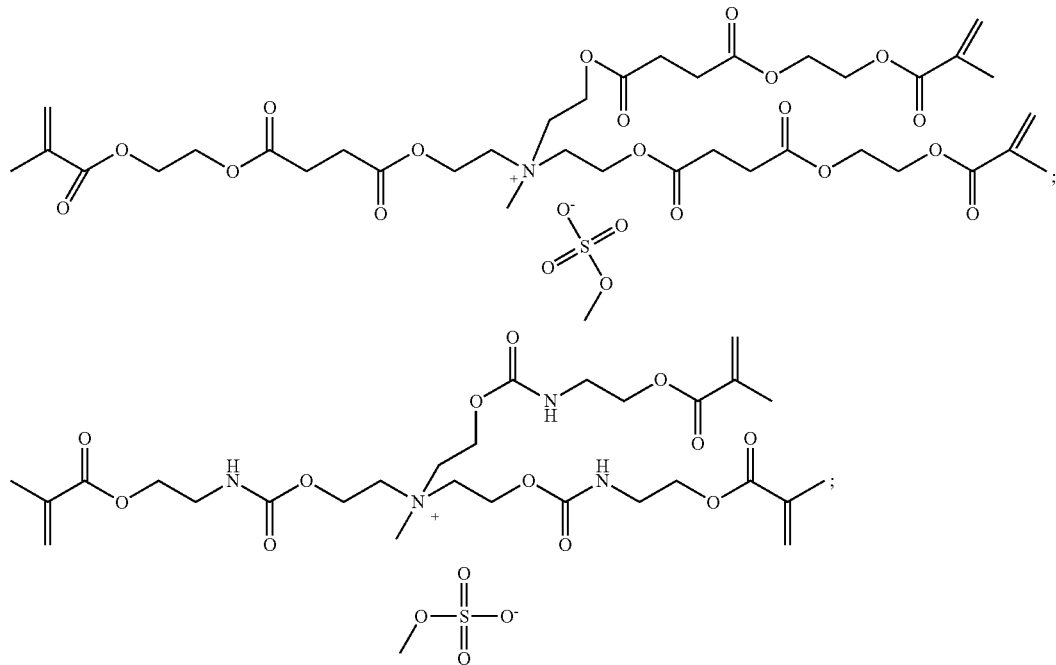

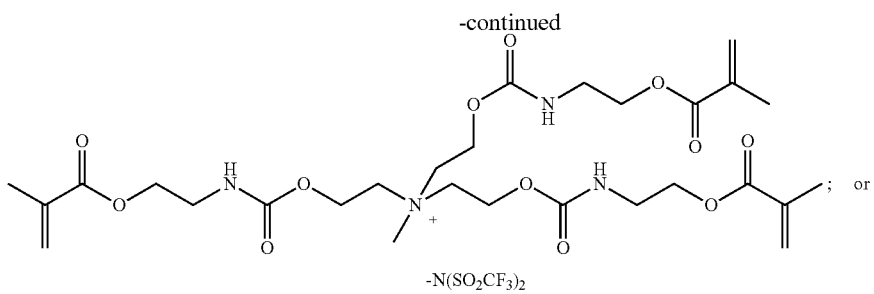

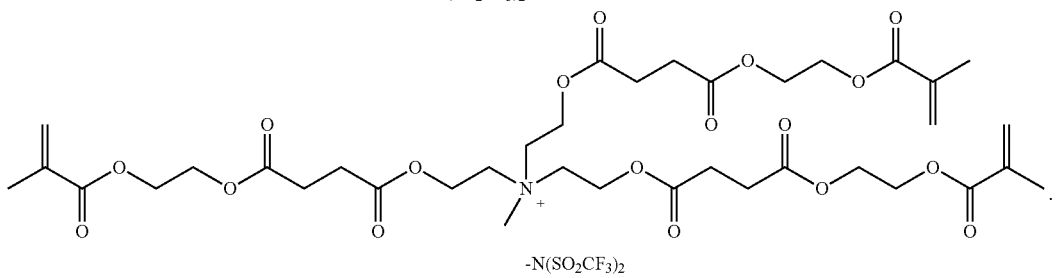

9. The coating composition of claim 1 wherein the multifunctional polymerizable ionic liquid has the formula

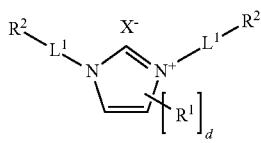

wherein:
- $R^1$ is independently comprises hydrogen, alkyl, aryl, alkaryl, or a combination thereof;
- $R^2$ is independently a (meth)acrylate group;
- $L^1$ is independently a linking groups with the proviso that at least two of the linking groups independently comprise one or more linkages selected from amide, urethane, urea, ether, or ester;
- d is an integer of 0 to 3;
- X is an anion.

10. The coating of claim 1 wherein the multifunctional polymerizable ionic liquid has the formula

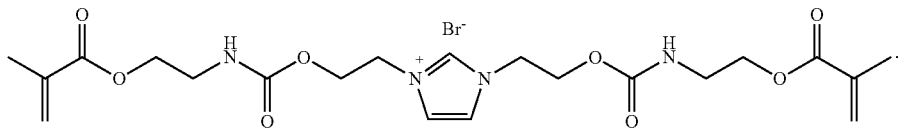

11. The coating of claim 1 wherein the monofunctional polymerizable ionic liquid has the formula:

$(R^1)_{a-b}G^+[(CH_2)_qDR^2]_b X^-$ wherein
- each $R^1$ comprises independently a hydrogen, alkyl, aryl, alkaryl, or a combination thereof;
- G is nitrogen, sulfur or phosphorous;
- a is 3 where G is sulfur and a is 4 where G is nitrogen or phosphorous;
- b is 1;
- q is an integer from 1 to 4;
- D is oxygen, sulfur, or NR wherein R is H or a lower alkyl of 1 to 4 carbon atoms;
- $R^2$ is a (meth)acryl; and
- X— is an anion.

12. The coating of claim 11 wherein G is nitrogen of an ammonium cation.

13. The coating of claim 11 wherein G is included in the cycle of an imidazolium cation and the monofunctional polymerizable liquid has the formula:

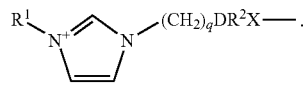

14. The coating of claim 11 wherein $R^2$ is (meth)acrylate and D is an oxygen atom of the (meth)acrylate group.

15. The coating of claim 11 wherein $R^1$ is a lower alkyl of 1 to 4 carbon atoms.

16. The coating of claim 11 wherein X is a halide or a fluororganic anion.

17. The coating of claim 1 wherein the coating is an antistatic coating.

18. A coated substrate comprising a substrate and the coating of claim 1 cured on a surface of the substrate.

* * * * *

UNITED STATES PATENT AND TRADEMARK OFFICE
CERTIFICATE OF CORRECTION

Page 1 of 2

PATENT NO.        : 8,742,047 B2
APPLICATION NO.   : 13/380252
DATED             : June 3, 2014
INVENTOR(S)       : Kevin Lewandowski et al.

It is certified that error appears in the above-identified patent and that said Letters Patent is hereby corrected as shown below:

On the Title Page, Item (56)

First Page, Column 2 (Other Publications)
Line 6, Delete "Evalutaion" and insert -- Evaluation --, therefor.
Line 12, Delete "Account" and insert -- Accounts --, therefor.

Page 2, Column 2 (Other Publications)
Line 1, Delete "0$_2$," and insert -- O$_2$, --, therefor.

Page 3, Column 1 (Other Publications)
Line 7, Delete "Acryalte" and insert -- Acrylate --, therefor.
Line 39, Delete "Tatrahedron" and insert -- Tetrahedron --, therefor.
Line 41, Delete "Surfact" and insert -- Surface --, therefor.

Page 3, Column 2 (Other Publications)
Line 1, Delete "Termally" and insert -- Thermally --, therefor.
Line 27, Delete "Electrom" and insert -- Electron --, therefor.

In the Specification

Column 4
Line 17, Delete "heteratoms" and insert -- heteroatoms --, therefor.

Column 10
Line 54, Delete "1-ethy" and insert -- 1-ethyl --, therefor.
Line 58, Delete "1-methylheptyamine" and insert -- 1- methylheptylamine --, therefor.

Signed and Sealed this
Seventh Day of April, 2015

Michelle K. Lee
*Director of the United States Patent and Trademark Office*

CERTIFICATE OF CORRECTION (continued)
U.S. Pat. No. 8,742,047 B2

Column 14
Line 21, Delete "tetrafluoroboarate" and insert -- tetrafluoroborate --, therefor.

Column 16
Line 44, Delete "then" and insert -- than --, therefor.

Column 16
Line 45, Delete "then" and insert -- than --, therefor.

Column 19
Line 59, Delete "pentaerthyritol" and insert -- pentaerythritol --, therefor.

Column 25
Line 19, Delete "the the" and insert -- the --, therefor.

Column 27
Line 12, Delete "absorbtion" and insert -- absorption --, therefor.

Column 29
Line 13, Delete "reparatory" and insert -- separatory --, therefor.
Line 47, Delete "reparatory" and insert -- separatory --, therefor.
Line 59, Delete "Light light" and insert -- Light --, therefor.